(12) United States Patent
Allen et al.

(10) Patent No.: US 8,653,105 B2
(45) Date of Patent: Feb. 18, 2014

(54) QUINOLINE DERIVATIVES AS KINASE INHIBITORS

(75) Inventors: Daniel Rees Allen, Saffron Walden Essex (GB); Roland Bürli, Saffron Walden Essex (GB); Alan Findlay Haughan, Saffron Walden Essex (GB); Mizio Matteucci, Saffron Walden Essex (GB); Andrew Pate Owens, Saffron Walden Essex (GB); Gilles Raphy, Saffron Walden Essex (GB); Andrew Sharpe, Saffron Walden Essex (GB)

(73) Assignee: UCB Pharma S.A., Brussels (BE)

( * ) Notice: Subject to any disclaimer, the term of this patent is extended or adjusted under 35 U.S.C. 154(b) by 97 days.

(21) Appl. No.: 13/508,956

(22) PCT Filed: Nov. 11, 2010

(86) PCT No.: PCT/EP2010/067304
§ 371 (c)(1),
(2), (4) Date: Sep. 24, 2012

(87) PCT Pub. No.: WO2011/058108
PCT Pub. Date: May 19, 2011

(65) Prior Publication Data
US 2013/0012517 A1     Jan. 10, 2013

(30) Foreign Application Priority Data

Nov. 12, 2009   (GB) .................................. 0919829.2
Jul. 19, 2010   (GB) .................................. 1012102.8

(51) Int. Cl.
*A61K 31/4709*   (2006.01)
*C07D 401/14*    (2006.01)
*C07D 215/50*    (2006.01)

(52) U.S. Cl.
USPC ........................... 514/314; 544/363; 546/152

(58) Field of Classification Search
None
See application file for complete search history.

(56) References Cited

U.S. PATENT DOCUMENTS

2009/0137581 A1   5/2009   Chen et al.

FOREIGN PATENT DOCUMENTS

WO   WO 2008118468 A1  *  10/2008

OTHER PUBLICATIONS

Morissette et al., High-throughput crystallization: polymorphs, salts, co-crystals and solvates of pharmaceutical solids, Advanced Drug Delivery Reviews 2004, 56, 275-300.*
Hamdi et al., Solvates of indomethacin. Journal of Thermal Analysis and Calorimetry 2004, 76, 985-1001.*

* cited by examiner

*Primary Examiner* — Jason M Nolan
*Assistant Examiner* — Ana Z Muresan
(74) *Attorney, Agent, or Firm* — McDonnell Boehnen Hulbert & Berghoff LLP

(57) ABSTRACT

A series of quinoline derivatives, substituted by an optionally substituted bicyclic heteroaryl moiety consisting of two fused six-membered aromatic rings attached via an alkylene chain optionally linked to a heteroatom, being selective inhibitors of PI3 kinase enzymes, are accordingly of benefit in medicine, for example in the treatment of inflammatory, autoimmune, cardiovascular, neurodegenerative, metabolic, oncological, nociceptive or ophthalmic conditions.

11 Claims, No Drawings

QUINOLINE DERIVATIVES AS KINASE INHIBITORS

This application is a U.S. national phase of International Application No. PCT/EP2010/067304 filed on Nov. 11, 2010, the disclosure of which is incorporated herein by reference in its entirety.

The present invention relates to a class of quinoline and quinoxaline derivatives, and to their use in therapy. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds in accordance with the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds in accordance with the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

WO 2008/118454, WO 2008/118455 and WO 2008/118468 describe various series of quinoline and quinoxaline derivatives that are structurally related to each other and are stated to be useful to inhibit the biological activity of human PI3Kδ and to be of use in treating PI3K-mediated conditions or disorders.

WO 2009/081105, copending international application PCT/GB2009/002504, published on 29 Apr. 2010 as WO 2010/046639 (claiming priority from United Kingdom patent application 0819593.5), copending international application PCT/GB2010/000243, published on 19 Aug. 2010 as WO 2010/092340 (claiming priority from United Kingdom patent applications 0902450.6 and 0914533.5), copending international application PCT/GB2010/000361, published on 10 Sep. 2010 as WO 2010/100405 (claiming priority from United Kingdom patent applications 0903949.6 and 0915586.2), and copending international application PCT/GB2010/001000 (claiming priority from United Kingdom patent application 0908957.4) describe separate classes of fused bicyclic heteroaryl derivatives as selective inhibitors of PI3K enzymes that are of benefit in the treatment of adverse inflammatory, autoimmune, cardiovascular, neurodegenerative, metabolic, oncological, nociceptive and ophthalmic conditions.

None of the prior art available to date, however, discloses or suggests the precise structural class of quinoline and quinoxaline derivatives as provided by the present invention.

The compounds of the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The present invention provides a compound of formula (I) or an N-oxide thereof, or a pharmaceutically acceptable salt or solvate thereof:

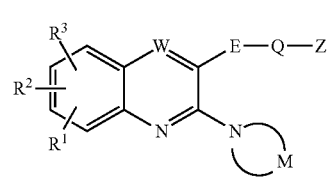

(I)

wherein

E represents an optionally substituted straight or branched $C_{1-4}$ alkylene chain;

Q represents oxygen, sulfur, N—$R^4$ or a covalent bond;

Z represents an optionally substituted bicyclic heteroaryl moiety consisting of two fused six-membered aromatic rings, the heteroaryl moiety Z containing at least one nitrogen atom and being linked to the remainder of the molecule through a carbon atom;

M represents the residue of an optionally substituted saturated five-, six- or seven-membered monocyclic ring containing one nitrogen atom and 0, 1, 2 or 3 additional heteroatoms independently selected from N, O and S, but containing no more than one O or S atom;

W represents C—$R^5$ or N;

$R^1$, $R^2$ and $R^3$ independently represent hydrogen, halogen, cyano, nitro, $C_{1-6}$ alkyl, trifluoromethyl, $C_{3-7}$ cycloalkyl($C_{1-6}$)alkyl, $C_{3-7}$ heterocycloalkyl($C_{1-6}$)alkyl, aryl($C_{1-6}$) alkyl, heteroaryl($C_{1-6}$)alkyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$) alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl or di(C$_{1-6}$)alkylaminosulfonyl;

R$^4$ represents hydrogen or C$_{1-6}$ alkyl; and

R$^5$ represents hydrogen, halogen, C$_{1-6}$ alkyl or C$_{1-6}$ alkoxy.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched C$_{1-6}$ alkyl groups, for example C$_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "C$_{1-6}$ alkoxy", "C$_{1-6}$ alkylthio", "C$_{1-6}$ alkylsulphonyl" and "C$_{1-6}$ alkylamino" are to be construed accordingly.

The expression "C$_{1-3}$ alkylene chain" refers to a divalent straight or branched alkylene chain containing 1 to 3 carbon atoms. Typical examples include methylene, ethylene, methylmethylene, ethylmethylene and dimethylmethylene.

Specific C$_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl(C$_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto (CH$_2$C=O)↔ enol (CH=CHOH) tautomers or amide (NHC=O)↔ hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1$H, $^2$H (deuterium) or $^3$H (tritium) atom, preferably $^1$H. Similarly, by way of example, each individual carbon atom present in formula (I), or in the formulae depicted hereinafter, may be present as a $^{12}$C, $^{13}$C or $^{14}$C atom, preferably $^{12}$C.

In one embodiment, W represents C—R$^5$. In another embodiment, W represents N.

Specific sub-classes of compounds in accordance with the present invention are represented by the compounds of formula (IA) and (IB), especially (IA):

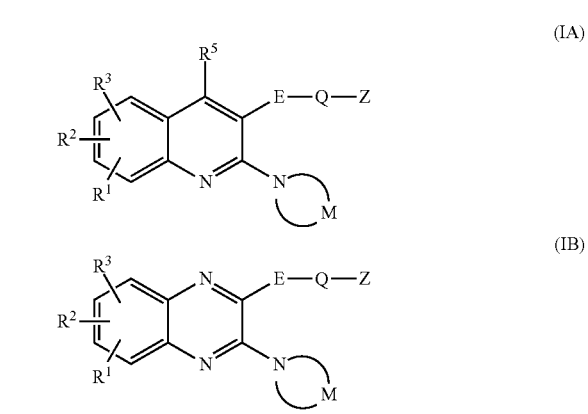

wherein E, Q, Z, M, R$^1$, R$^2$, R$^3$ and R$^5$ are as defined above.

Typical values of E include methylene (—CH$_2$—), (methyl)methylene, ethylene (—CH$_2$CH$_2$—), (ethyl)methylene, (dimethyl)methylene, (methyl)ethylene, (propyl)methylene and (dimethyl)ethylene, any of which chains may be optionally substituted by one or more substituents. Suitably, such chains are unsubstituted, monosubstituted or disubstituted. Preferably, such chains are unsubstituted or monosubstituted. In one embodiment, such chains are unsubstituted. In another embodiment, such chains are monosubstituted.

Examples of suitable substituents on the alkylene chain represented by E include trifluoromethyl, C$_{3-7}$ heterocycloalkyl, aryl, oxo, hydroxy, C$_{1-6}$ alkoxy, C$_{2-6}$ alkoxycarbonyl(C$_{1-6}$)alkoxy, aminocarbonyl(C$_{1-6}$)alkoxy, trifluoromethoxy, amino, C$_{1-6}$ alkylamino, di(C$_{1-6}$)alkylamino, aminocarbonyl, C$_{1-6}$ alkylaminocarbonyl and di(C$_{1-6}$)alkylaminocarbonyl.

Examples of particular substituents on the alkylene chain represented by E include trifluoromethyl, pyrrolidinyl, piperidinyl, piperazinyl, morpholinyl, phenyl, oxo, hydroxy, ethoxy, ethoxycarbonylmethoxy, aminocarbonylmethoxy, trifluoromethoxy, amino, methylamino, dimethylamino, aminocarbonyl, methylaminocarbonyl and dimethylaminocarbonyl.

Suitable values of E include methylene (—CH$_2$—) and (methyl)methylene.

A particular value of E is (methyl)methylene, i.e. —CH(CH$_3$)—.

Another value of E is methylene, i.e. —CH$_2$—.

Suitable values of Q include oxygen and N—R$^4$.

In one embodiment, Q represents oxygen. In another embodiment, Q represents sulfur. In a further embodiment, Q represents N—R$^4$. In a still further embodiment, Q represents a covalent bond.

Generally, the bicyclic heteroaryl moiety Z contains one, two, three or four nitrogen atoms and no other heteroatoms. Typically, Z contains two, three or four nitrogen atoms. Suitably, Z contains two or three nitrogen atoms.

In one embodiment, Z contains one nitrogen atom. In another embodiment, Z contains two nitrogen atoms. In another embodiment, Z contains three nitrogen atoms. In a further embodiment, Z contains four nitrogen atoms.

Typical values for the heteroaryl moiety Z include quinolinyl, isoquinolinyl, cinnolinyl, quinazolinyl, quinoxalinyl, phthalazinyl, naphthyridinyl, pyrido-pyrimidinyl and pteridinyl, any of which groups may be optionally substituted by one or more substituents.

Suitable values of Z include quinolinyl, quinoxalinyl, naphthyridinyl and pyrido-pyrimidinyl, any of which groups may be optionally substituted by one or more substituents.

Selected values of Z include naphthyridinyl and pyrido-pyrimidinyl, either of which groups may be optionally substituted by one or more substituents.

In one embodiment, Z represents optionally substituted naphthyridinyl. In one aspect of that embodiment, Z represents optionally substituted 1,5-naphthyridin-4-yl.

In one embodiment, Z represents optionally substituted pyrido-pyrimidinyl. In one aspect of that embodiment, Z represents optionally substituted pyrido[2,3-d]pyrimidin-4-yl. In another aspect of that embodiment, Z represents optionally substituted pyrido[3,2-d]pyrimidin-4-yl. In a further aspect of that embodiment, Z represents optionally substituted pyrido[3,4-d]pyrimidin-4-yl.

In one embodiment, the heteroaryl moiety Z is unsubstituted. In another embodiment, Z is substituted by one or more substituents. In one subset of that embodiment, Z is monosubstituted. In another subset of that embodiment, Z is disubstituted.

Typical examples of optional substituents on the heteroaryl moiety Z include one or more substituents independently selected from halogen, cyano, nitro, C$_{1-6}$ alkyl, trifluoromethyl, hydroxy, oxo, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkylamino, arylamino, C$_{1-6}$ alkoxyaryl(C$_{1-6}$)alkylamino, C$_{2-6}$ alkylcarbonylamino, C$_{1-6}$ alkylsulfonylamino, formyl, C$_{2-6}$ alkylcarbonyl, C$_{3-6}$ cycloalkylcarbonyl, C$_{3-6}$ heterocycloalkylcarbonyl, carboxy, C$_{2-6}$ alkoxycarbonyl, aminocarbonyl, C$_{1-6}$ alkylaminocarbonyl, di(C$_{1-6}$)alkylaminocarbonyl, aminosulfonyl, C$_{1-6}$ alkylaminosulfonyl and di(C$_{1-6}$)alkylaminosulfonyl.

Typical examples of specific substituents on Z include fluoro, chloro, bromo, cyano, nitro, methyl, isopropyl, trifluoromethyl, hydroxy, oxo, methoxy, difluoromethoxy, trifluoromethoxy, methylthio, methylsulfinyl, methylsulfonyl, amino, methylamino, tert-butylamino, dimethylamino, phenylamino, methoxybenzylamino, acetylamino, methoxycarbonylamino, methylsulfonylamino, formyl, acetyl, cyclopropylcarbonyl, azetidinylcarbonyl, N-methylazetidinylcarbonyl, pyrrolidinylcarbonyl, N-methylpyrrolidinylcarbonyl, piperidinylcarbonyl, N-methylpiperidinylcarbonyl, piperazinylcarbonyl, N-methylpiperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Typical specific values of Z include 1,5-naphthyridin-4-yl, pyrido[2,3-d]-pyrimidin-4-yl and pyrido[3,2-d]pyrimidin-4-yl.

In one embodiment, M represents the residue of an optionally substituted saturated five-membered monocyclic ring. In another embodiment, M represents the residue of an optionally substituted saturated six-membered monocyclic ring. In a further embodiment, M represents the residue of an optionally substituted saturated seven-membered monocyclic ring.

In one embodiment, the monocyclic ring of which M is the residue contains one nitrogen atom and no additional heteroatoms (i.e. it is an optionally substituted pyrrolidin-1-yl, piperidin-1-yl or hexahydroazepin-1-yl ring). In another embodiment, the monocyclic ring of which M is the residue contains one nitrogen atom and one additional heteroatom selected from N, O and S. In a further embodiment, the monocyclic ring of which M is the residue contains one nitrogen atom and two additional heteroatoms selected from N, O and S, of which not more than one is O or S. In a still further embodiment, the monocyclic ring of which M is the residue contains one nitrogen atom and three additional heteroatoms selected from N, O and S, of which not more than one is O or S.

Typical values of the monocyclic ring of which M is the residue include pyrrolidin-1-yl, imidazolidin-1-yl, piperidin-1-yl, morpholin-4-yl, thiomorpholin-4-yl, piperazin-1-yl and [1,4]diazepan-1-yl, any of which rings may be optionally substituted by one or more substituents.

Selected values of the monocyclic ring of which M is the residue include pyrrolidin-1-yl, piperidin-1-yl and piperazin-1-yl, any of which rings may be optionally substituted by one or more substituents.

Suitable values of the monocyclic ring of which M is the residue include pyrrolidin-1-yl and piperazin-1-yl, either of which rings may be optionally substituted by one or more substituents.

A particular value of the monocyclic ring of which M is the residue is optionally substituted piperazin-1-yl.

In one embodiment, the monocyclic ring of which M is the residue is unsubstituted. In another embodiment, the monocyclic ring of which M is the residue is substituted by one or more substituents. In one subset of that embodiment, the monocyclic ring of which M is the residue is monosubstituted. In another subset of that embodiment, the monocyclic ring of which M is the residue is disubstituted.

Typical examples of suitable substituents on the monocyclic ring of which M is the residue include halogen, $C_{1-6}$ alkyl, heteroaryl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, cyano, trifluoromethyl, oxo, $C_{2-6}$ alkylcarbonyl, ($C_{3-7}$)cycloalkylcarbonyl, ($C_{3-7}$)heterocycloalkylcarbonyl($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, amino, amino($C_{1-6}$)alkyl, $C_{1-6}$ alkylamino, di($C_{1-6}$)alkylamino, phenylamino, pyridinylamino, $C_{2-6}$ alkylcarbonylamino, hydroxy($C_{1-6}$)alkylcarbonylamino, ($C_{3-7}$)cycloalkylcarbonylamino, $C_{2-6}$ alkoxycarbonylamino, $C_{1-6}$ alkylsulphonylamino, aminocarbonyl, $C_{1-6}$ alkylaminocarbonyl, di($C_{1-6}$)alkylaminocarbonyl and di($C_{1-6}$)alkylaminocarbonyl($C_{1-6}$)alkyl. Additional examples include hydroxy($C_{1-6}$)alkylcarbonyl, di($C_{1-6}$)alkylamino($C_{1-6}$)alkylcarbonyl, aminocarbonyl($C_{1-6}$)alkyl and ($C_{1-6}$)alkylaminocarbonyl($C_{1-6}$)alkyl.

Selected examples of suitable substituents on the monocyclic ring of which M is the residue include heteroaryl, hydroxy, hydroxy($C_{1-6}$)alkyl, oxo, $C_{2-6}$ alkylcarbonyl, hydroxy($C_{1-6}$)alkylcarbonyl, di($C_{1-6}$)alkylamino($C_{1-6}$)alkylcarbonyl, ($C_{3-7}$)cycloalkylcarbonyl, carboxy, carboxy($C_{1-6}$)alkyl, $C_{2-6}$ alkoxycarbonyl, hydroxy($C_{1-6}$)alkylcarbonylamino, ($C_{3-7}$)cycloalkylcarbonylamino, aminocarbonyl, aminocarbonyl($C_{1-6}$)alkyl, $C_{1-6}$ alkylaminocarbonyl and ($C_{1-6}$)alkylaminocarbonyl($C_{1-6}$)alkyl.

Illustrative examples of suitable substituents on the monocyclic ring of which M is the residue include heteroaryl, hydroxy($C_{1-6}$)alkyl, oxo, $C_{2-6}$ alkylcarbonyl, carboxy($C_{1-6}$)alkyl, $C_{2-6}$ alkoxycarbonyl, hydroxy($C_{1-6}$)alkylcarbonylamino and ($C_{3-7}$)cycloalkylcarbonylamino.

Typical examples of specific substituents on the monocyclic ring of which M is the residue include fluoro, chloro, bromo, methyl, ethyl, isopropyl, pyridinyl, pyrazinyl, methoxy, isopropoxy, difluoromethoxy, trifluoromethoxy, methoxymethyl, methylthio, ethylthio, methylsulphonyl, hydroxy, hydroxymethyl, hydroxyethyl, cyano, trifluoromethyl, oxo, acetyl, ethylcarbonyl, tert-butylcarbonyl, cyclopropylcarbonyl, morpholinylcarbonylmethyl, carboxy, carboxymethyl, methoxycarbonyl, ethoxycarbonyl, tert-butoxycarbonyl, methoxycarbonylmethyl, ethoxycarbonylmethyl, amino, aminomethyl, methylamino, ethylamino, dimethylamino, phenylamino, pyridinylamino, acetylamino, hydroxyacetylamino, cyclopropylcarbonylamino, tert-butoxycarbonylamino, methylsulphonylamino, aminocarbonyl, methylaminocarbonyl, dimethylaminocarbonyl and dimethylaminocarbonylmethyl. Additional examples include hydroxyacetyl, dimethylaminoacetyl, aminocarbonylmethyl and methylaminocarbonylmethyl.

Selected examples of specific substituents on the monocyclic ring of which M is the residue include pyridinyl, pyrazinyl, hydroxy, hydroxyethyl, oxo, acetyl, ethylcarbonyl, tert-butylcarbonyl, hydroxyacetyl, dimethylaminoacetyl, cyclopropylcarbonyl, carboxy, carboxymethyl, methoxycarbonyl, hydroxyacetylamino, cyclopropylcarbonylamino, aminocarbonyl, aminocarbonylmethyl, methylaminocarbonyl and methylaminocarbonylmethyl.

Illustrative examples of specific substituents on the monocyclic ring of which M is the residue include pyridinyl, pyrazinyl, hydroxyethyl (especially 2-hydroxyethyl), oxo, acetyl, ethylcarbonyl, tert-butylcarbonyl, carboxymethyl, methoxycarbonyl, hydroxyacetylamino and cyclopropylcarbonylamino.

A particular substituent on the monocyclic ring of which M is the residue is oxo.

Typical values of the monocyclic ring of which M is the residue include pyrrolidin-1-yl, 3-hydroxypyrrolidin-1-yl, 3-(acetylamino)pyrrolidin-1-yl, 3-(hydroxyacetylamino)pyrrolidin-1-yl, 3-(cyclopropylcarbonylamino)pyrrolidin-1-yl, imidazolidin-1-yl, 4-(acetylamino)piperidin-1-yl, 4-(methylsulphonylamino)piperidin-1-yl, morpholin-4-yl, 3-methylmorpholin-4-yl, thiomorpholin-4-yl, 1,1-dioxothiomorpholin-4-yl, piperazin-1-yl, 4-(pyridin-2-yl)piperazin-1-yl, 4-(pyrazin-2-yl)piperazin-1-yl, 4-(methylsulphonyl)piperazin-1-yl, 4-(2-hydroxyethyl)piperazin-1-yl, 3-oxopiperazin-1-yl, 4-methyl-3-oxopiperazin-1-yl, 4-acetylpiperazin-1-yl, 4-(ethylcarbonyl)piperazin-1-yl, 4-(tert-butylcarbonyl)piperazin-1-yl, 4-(cyclopropylcarbonyl)piperazin-1-yl, 4-(morpholin-4-ylcarbonylmethyl)piperazin-1-yl, 4-(carboxymethyl)piperazin-1-yl, 4-(methoxycarbonyl)piperazin-1-yl, 4-(ethoxycarbonylmethyl)piperazin-1-yl, 4-(dimethylaminocarbonylmethyl)piperazin-1-yl and 5-oxo-[1,4]diazepan-1-yl. Additional examples include 4-hydroxypiperidin-1-yl, 4-carboxypiperidin-1-yl, 4-(aminocarbonyl)piperidin-1-yl, 4-(methylaminocarbonyl)piperidin-1-yl, 4-(hydroxyacetyl)piperazin-1-yl, 4-(dimethylaminoacetyl)piperazin-1-yl, 4-(aminocarbonyl)piperazin-1-yl, 4-(aminocarbonylmethyl)piperazin-1-yl and 4-(methylaminocarbonylmethyl)piperazin-1-yl.

Selected values of the monocyclic ring of which M is the residue include 3-(hydroxyacetylamino)pyrrolidin-1-yl, 3-(cyclopropylcarbonylamino)pyrrolidin-1-yl, 4-hydroxypiperidin-1-yl, 4-carboxypiperidin-1-yl, 4-(aminocarbonyl)piperidin-1-yl, 4-(methylaminocarbonyl)piperidin-1-yl, 4-(pyridin-2-yl)piperazin-1-yl, 4-(pyrazin-2-yl)piperazin-1-yl, 4-(2-hydroxyethyl)piperazin-1-yl, 3-oxopiperazin-1-yl, 4-acetylpiperazin-1-yl, 4-(ethylcarbonyl)piperazin-1-yl, 4-(tert-butylcarbonyl)piperazin-1-yl, 4-(hydroxyacetyl)piperazin-1-yl, 4-(dimethylaminoacetyl)piperazin-1-yl, 4-(cyclopropylcarbonyl)piperazin-1-yl, 4-(carboxymethyl)piperazin-1-yl, 4-(methoxycarbonyl)piperazin-1-yl, 4-(aminocarbonyl)piperazin-1-yl, 4-(aminocarbonylmethyl)piperazin-1-yl and 4-(methylaminocarbonylmethyl)piperazin-1-yl.

Particular values of the monocyclic ring of which M is the residue include 3-(hydroxyacetylamino)pyrrolidin-1-yl, 3-(cyclopropylcarbonylamino)pyrrolidin-1-yl, 4-(pyridin-2-yl)piperazin-1-yl, 4-(pyrazin-2-yl)piperazin-1-yl, 4-(2-hydroxyethyl)piperazin-1-yl, 3-oxopiperazin-1-yl, 4-acetylpiperazin-1-yl, 4-(ethylcarbonyl)piperazin-1-yl, 4-(tert-butylcarbonyl)piperazin-1-yl, 4-(carboxymethyl)piperazin-1-yl and 4-(methoxycarbonyl)piperazin-1-yl.

A favoured value of the monocyclic ring of which M is the residue is 3-oxo-piperazin-1-yl.

Typical values of $R^1$, $R^2$ and/or $R^3$ include hydrogen, halogen, $C_{1-6}$ alkyl, aryl($C_{1-6}$)alkyl and $C_{1-6}$ alkoxy.

Suitably, $R^1$, $R^2$ and $R^3$ independently represent hydrogen, fluoro, chloro, bromo, cyano, nitro, methyl, ethyl, trifluoromethyl, benzyl, hydroxy, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl or dimethylaminosulfonyl.

Typically, $R^1$ represents hydrogen, halogen, $C_{1-6}$ alkyl, aryl($C_{1-6}$)alkyl or $C_{1-6}$ alkoxy.

Illustrative values of $R^1$ include hydrogen, halogen and $C_{1-6}$ alkyl.

In one embodiment, $R^1$ represents hydrogen. In another embodiment, $R^1$ represents halogen, particularly fluoro or chloro. In one aspect of that embodiment, $R^1$ represents fluoro. In another aspect of that embodiment, $R^1$ represents chloro. In a further embodiment, $R^1$ represents $C_{1-6}$ alkyl, particularly methyl or ethyl. In one aspect of that embodiment, $R^1$ represents methyl. In another aspect of that embodiment, $R^1$ represents ethyl. In a still further embodiment, $R^1$ represents aryl($C_{1-6}$)alkyl, especially benzyl. In an additional embodiment, $R^1$ represents $C_{1-6}$ alkoxy, especially methoxy.

Typically, $R^2$ represents hydrogen or halogen.

In one embodiment, $R^2$ represents hydrogen. In another embodiment, $R^2$ represents halogen, particularly fluoro or chloro. In one aspect of that embodiment, $R^2$ represents fluoro. In another aspect of that embodiment, $R^2$ represents chloro.

Typically, $R^3$ represents hydrogen.

In a particular embodiment, $R^2$ and $R^3$ both represent hydrogen.

In one embodiment, $R^4$ represents hydrogen. In another embodiment, $R^4$ represents $C_{1-6}$ alkyl, especially methyl.

Suitable values of the group $R^4$ include hydrogen and methyl.

Typically, $R^5$ represents hydrogen or $C_{1-6}$ alkyl.

In one embodiment, $R^5$ represents hydrogen. In another embodiment, $R^5$ represents halogen, particularly fluoro or chloro. In one aspect of that embodiment, $R^5$ represents fluoro. In another aspect of that embodiment, $R^5$ represents chloro. In a further embodiment, $R^5$ represents $C_{1-6}$ alkyl, especially methyl. In an additional embodiment, $R^5$ represents $C_{1-6}$ alkoxy, especially methoxy.

Suitable values of the group $R^5$ include hydrogen, fluoro, chloro, bromo, methyl and methoxy. Suitably, $R^5$ represents hydrogen or methyl. Typically, $R^5$ represents hydrogen.

One sub-class of compounds according to the invention is represented by the compounds of formula (IIA) and N-oxides thereof, and pharmaceutically acceptable salts and solvates thereof:

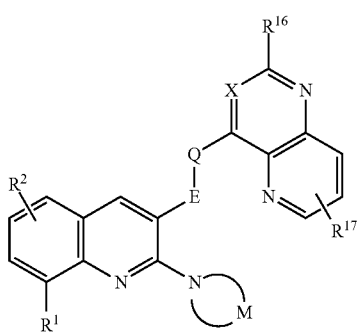

(IIA)

wherein E, Q, M, $R^1$ and $R^2$ are as defined above;

X represents N or CH; and $R^{16}$ and $R^{17}$ independently represent hydrogen, $C_{1-6}$ alkyl, amino, $C_{1-6}$ alkylamino or di($C_{1-6}$)alkylamino.

In one embodiment, X is N. In another embodiment, X is CH.

Typical values of $R^{16}$ include hydrogen, methyl, ethyl, isopropyl, amino, methylamino, ethylamino, tert-butylamino and dimethylamino.

A particular value of $R^{16}$ is hydrogen.

Typical values of $R^{17}$ include hydrogen, methyl, ethyl, isopropyl, amino, methylamino, ethylamino, tert-butylamino and dimethylamino.

A particular value of $R^{17}$ is hydrogen.

Another sub-class of compounds according to the invention is represented by the compounds of formula (IIB) and N-oxides thereof, and pharmaceutically acceptable salts and solvates thereof:

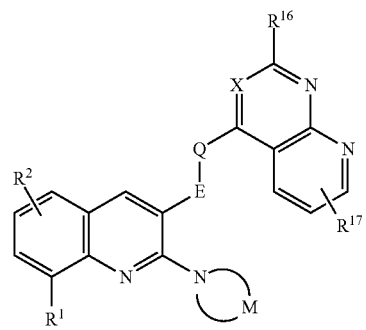

(IIB)

wherein E, Q, M, $R^1$, $R^2$, X, $R^{16}$ and $R^{17}$ are as defined above.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above wherein Q represents oxygen, sulphur or N—$R^4$ may be prepared by a process which comprises reacting a compound of formula (III) with a compound of formula (IV):

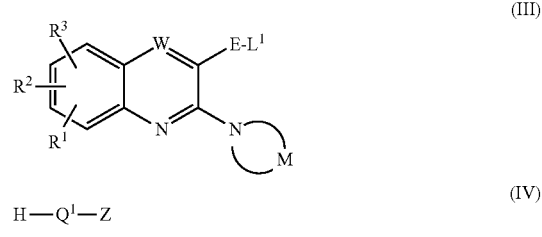

wherein $Q^1$ represents oxygen, sulphur or N—$R^4$, $L^1$ represents a suitable leaving group, and E, Z, M, W, $R^1$, $R^2$, $R^3$ and $R^4$ are as defined above.

The leaving group $L^1$ is typically a halogen atom, e.g. bromo or iodo.

The reaction is conveniently effected at ambient or elevated temperature in a suitable solvent, e.g. N,N-dimethylformamide or acetonitrile. The reaction may be performed in the presence of a suitable base, e.g. an inorganic base such as potassium carbonate, cesium carbonate, sodium hydride or aqueous sodium hydroxide.

The intermediates of formula (III) above wherein $L^1$ is bromo or iodo may be prepared from a compound of formula (V):

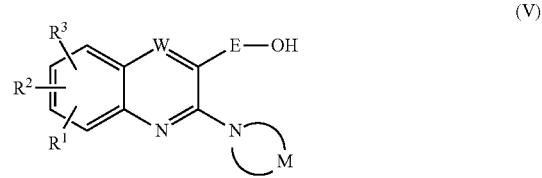

wherein E, M, W, $R^1$, $R^2$ and $R^3$ are as defined above; by bromination or iodination.

The bromination reaction is conveniently effected by stirring compound (V) with an appropriate brominating agent, e.g. phosphorus tribromide, in a suitable solvent, e.g. a halogenated hydrocarbon such as dichloromethane.

The iodination reaction is conveniently effected by stirring compound (V) with an appropriate iodinating agent, e.g. elemental iodine, in a suitable solvent, e.g. a halogenated hydrocarbon such as dichloromethane, typically in the presence of triphenylphosphine and imidazole.

Alternatively, the intermediates of formula (III) above wherein E represents methylene and $L^1$ is bromo may be prepared from a compound of formula (VI):

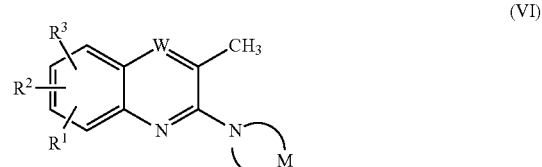

wherein M, W, $R^1$, $R^2$ and $R^3$ are as defined above; by bromination.

The reaction is conveniently effected at an elevated temperature in a suitable solvent, e.g. a halogenated solvent such as carbon tetrachloride, in the presence of a suitable brominating agent, e.g. N-bromosuccinimide, typically in the presence of a catalyst such as benzoyl peroxide.

In another procedure, the compounds of formula (I) wherein Q represents oxygen may be prepared by a process which comprises reacting a compound of formula (V) as defined above with a compound of formula (VII):

L²-Z  (VII)

wherein Z is as defined above, and L² represents a suitable leaving group.

The leaving group L² is typically a halogen atom, e.g. chloro.

The reaction is conveniently effected by stirring compounds (V) and (VII) at an elevated temperature in a suitable solvent, e.g. N,N-dimethylformamide or 1,4-dioxane, typically under basic conditions, e.g. in the presence of an inorganic base such as sodium hydride.

In another procedure, the compounds of formula (I) wherein Q represents sulfur may be prepared by a process which comprises reacting a compound of formula (VII) as defined above with a compound of formula (VIII):

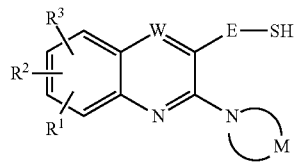

(VIII)

wherein E, M, W, R¹, R² and R³ are as defined above.

The reaction is conveniently effected by stirring compounds (VII) and (VIII) in a suitable solvent, e.g. a lower alkanol such as methanol, typically under basic conditions, e.g. in the presence of an alkali metal alkoxide such as sodium methoxide.

The intermediates of formula (VIII) may typically be prepared by treating a suitable compound of formula (III) above with thiolacetic acid; followed by treatment of the resulting compound with a base, e.g. an alkali metal alkoxide such as sodium methoxide.

In another procedure, the compounds of formula (I) wherein Q represents N—R⁴ may be prepared by a process which comprises reacting a compound of formula (VII) as defined above with a compound of formula (IX):

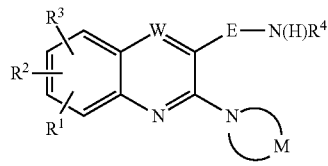

(IX)

wherein E, M, W, R¹, R², R³ and R⁴ are as defined above.

The reaction is conveniently effected at an elevated temperature in a suitable solvent, e.g. tetrahydrofuran, n-butanol, 1-methyl-2-pyrrolidinone (NMP) or 1,4-dioxane. The reaction may be performed in the presence of a suitable base, e.g. an organic base such as N,N-diisopropylethylamine.

The intermediates of formula (IX) wherein R⁴ represents hydrogen may be prepared by treating a suitable compound of formula (III) above with potassium phthalimide; followed by treatment of the resulting compound with hydrazine. Alternatively, they may be prepared by treating a suitable compound of formula (III) above with sodium azide; followed by treatment of the resulting compound with triphenylphosphine In an additional procedure, the compounds of formula (I) wherein E represents methylene and Q represents N—R⁴ may be prepared by a process which comprises reacting a compound of formula (IV) wherein Q¹ represents N—R⁴ with a compound of formula (X):

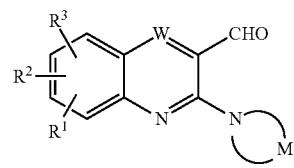

(X)

wherein M, W, R¹, R² and R³ are as defined above; under reducing conditions.

The reaction is conveniently effected by stirring the reactants at an elevated temperature in a suitable solvent, e.g. a cyclic ether such as tetrahydrofuran, in the presence of a reducing agent. A suitable reducing agent comprises a mixture of di-n-butyltin dichloride and phenylsilane.

The intermediates of formula (IX) wherein E represents methylene and R⁴ represents C₁₋₆ alkyl, e.g. methyl, may be prepared by treating a suitable compound of formula (X) above with a C₁₋₆ alkylamine, e.g. methylamine, in the presence of titanium(IV) n-propoxide and a base, e.g. an organic base such as N,N-diisopropylamine; followed by treatment of the resulting compound with a reducing agent, e.g. sodium triacetoxyborohydride.

The intermediates of formula (V) wherein E represents methylene may be prepared from the corresponding compound of formula (X) by treatment with a reducing agent, e.g. sodium borohydride.

The intermediates of formula (V), (VIII) and (IX) may be prepared by reacting a compound of formula (XI) with a compound of formula (XII):

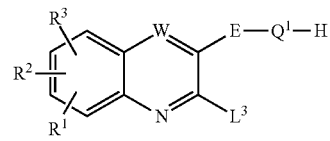

(XI)

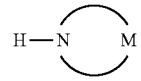

(XII)

wherein E, Q¹, M, W, R¹, R² and R³ are as defined above, and L³ represents a suitable leaving group.

The leaving group L³ is typically a halogen atom, e.g. chloro.

The reaction is conveniently effected at an elevated temperature in a suitable solvent, e.g. tetrahydrofuran, n-butanol, 1-methyl-2-pyrrolidinone (NMP) or ethylene glycol dimethyl ether (DME). The reaction may be performed in the presence of a suitable base, e.g. an organic base such as N,N-diisopropylethylamine.

The intermediates of formula (XI) wherein E represents (methyl)methylene and $Q^1$ represents NH may be prepared by a three-step procedure which comprises: (i) treating a suitable compound of formula (XIII):

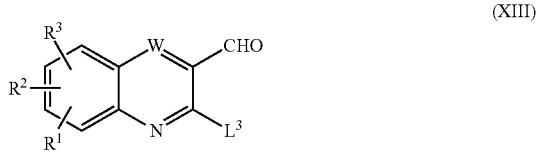

(XIII)

wherein W, $R^1$, $R^2$, $R^3$ and $L^3$ are as defined above; with 2-methyl-2-propanesulfinamide in the presence of titanium (IV) isopropoxide; (ii) reaction of the resulting compound with a Grignard reagent, e.g. methylmagnesium bromide; and (iii) treatment of the resulting compound with a mineral acid, e.g. hydrochloric acid.

Similarly, the intermediates of formula (XI) wherein E represents methylene and $Q^1$ represents NH may be prepared by a three-step procedure which comprises: (i) treating a suitable compound of formula (XIII) above with 2-methyl-2-propanesulfinamide in the presence of titanium(IV) isopropoxide; (ii) reaction of the resulting compound with a reducing reagent, e.g. sodium borohydride; and (iii) treatment of the resulting compound with a mineral acid, e.g. hydrochloric acid.

Where they are not commercially available, the starting materials of formula (IV), (VI), (VII), (X), (XII) and (XIII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of illustration, a compound of formula (I) wherein the monocyclic ring of which M is the residue is substituted by $C_{2-6}$ alkoxycarbonyl, e.g. methoxycarbonyl, or $C_{2-6}$ alkoxycarbonyl($C_{1-6}$)alkyl, e.g. ethoxycarbonylmethyl, may be converted into the corresponding compound wherein the monocyclic ring of which M is the residue is substituted respectively by carboxy or carboxy($C_{1-6}$)alkyl, e.g. carboxymethyl, by treatment with a base, typically an inorganic base, e.g. an alkali metal hydroxide such as sodium hydroxide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 µM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the $IC_{50}$.

When tested in the above assay, the compounds of the accompanying Examples were all found to possess $IC_{50}$ values for inhibition of activity of human PI3Kα and/or PI3Kβ and/or PI3Kγ and/or PI3Kδ of 50 µM or better.

EXAMPLES

Abbreviations

| | |
|---|---|
| DCM: | dichloromethane |
| DIPEA: | N,N-diisopropylethylamine |
| MeOH: | methanol |
| n-BuOH: | n-butanol |
| THF: | tetrahydrofuran |
| NMP: | 1-methyl-2-pyrrolidinone |
| Me: | methyl |
| DMF: | N,N-dimethylformamide |
| r.t.: | room temperature |
| $SiO_2$: | silica |
| br: | broad |
| HPLC: | High Performance Liquid Chromatography |
| LCMS: | Liquid Chromatography Mass Spectrometry |
| ES+: | Electrospray Positive Ionisation |

| | |
|---|---|
| Et$_2$O: | diethyl ether |
| EtOAc: | ethyl acetate |
| EtOH: | ethanol |
| Et$_3$N: | triethylamine |
| TFA: | trifluoroacetic acid |
| DME: | ethylene glycol dimethyl ether |
| MeCN: | acetonitrile |
| DMSO: | dimethylsulfoxide |
| RT: | retention time |
| h: | hour |
| M: | mass |

Analytical Conditions

All NMRs were obtained at 400 MHz.

Compounds were named with the aid of the Cambridgesoft Chemistry Cartridge (v. 9.0.0.182) software.

All reactions involving air- or moisture-sensitive reagents were performed under a nitrogen atmosphere using dried solvents and glassware.

| Analytical Condition | Method | Description | |
|---|---|---|---|
| 10 cm_ESCI_AmmBicarb_MeCN<br>10 cm_ESCI_Bicarb_MeCN | 1 | Solvents: | Acetonitrile (far UV grade)<br>Water (high purity via PureLab Option unit) with 10 mM ammonium hydrogencarbonate |
| 10 cm_ESI_Bicarb<br>10 cm_ESI_Bicarb_MeCN<br>10 cm_APCI_Formic | | Column: | Waters Xterra MS 5 µm C18, 100 × 4.6 mm (Plus guard cartridge) |
| | | Flow Rate: | 2 mL/min |
| | | Gradient: | A: Water/Bicarb<br>B: MeCN |

| Time | A % | B % |
|---|---|---|
| 0.00 | 95 | 5 |
| 0.50 | 95 | 5 |
| 4.00 | 5 | 95 |
| 5.50 | 5 | 95 |
| 5.60 | 95 | 5 |
| 6.50 | 95 | 5 |

| Analytical Condition | Method | Description | |
|---|---|---|---|
| 10 cm_ESI_Formic<br>10 cm_ESI_Formic_MeCN | 2 | Solvents: | Acetonitrile (far UV grade) with 0.1% (v/v) formic acid<br>Water (high purity via PureLab Option unit) with 0.1% formic acid |
| | | Column: | Phenomenex Luna 5 µm C18 (2), 100 × 4.6 mm (Plus guard cartridge) |
| | | Flow Rate: | 2 mL/min |
| | | Gradient: | A: Water/formic acid<br>B: MeCN/formic acid |

| Time | A % | B % |
|---|---|---|
| 0.00 | 95 | 5 |
| 3.50 | 5 | 95 |
| 5.50 | 5 | 95 |
| 5.60 | 95 | 5 |
| 6.50 | 95 | 5 |

| Analytical Condition | Method | Description | |
|---|---|---|---|
| 15 cm_Formic_Ascentis_HPLC_CH3CN | 3 | Solvents: | Acetonitrile (far UV grade) with 0.1% (v/v) formic acid<br>Water (high purity via PureLab Ultra unit) with 0.1% formic acid |
| | | Column: | Supelco, Ascentis ® Express C18, 2.7 µm C18, 150 × 4.6 mm |
| | | Flow Rate: | 1 mL/min |
| | | Gradient: | A: Water/formic acid<br>B: MeCN/formic acid |

| Time | A % | B % |
|---|---|---|
| 0.00 | 96 | 4 |
| 3.00 | 96 | 4 |
| 9.00 | 0 | 100 |
| 13.6 | 0 | 100 |
| 13.7 | 96 | 4 |
| 15.0 | 96 | 4 |

| Analytical Condition | Method | Description | |
|---|---|---|---|
| 10 cm_Formic_Ascentis_7 min_CH3CN | 4 | Solvents: | Acetonitrile (LC-MS grade) with 0.1% (v/v) formic acid<br>Water (high purity via PureLab Option unit) with 0.1% formic acid |
| | | Column: | Supelco, Ascentis ® Express 2.7 µm C18, 100 × 4.6 mm |

| Analytical Condition | Method | Description |
|---|---|---|
| | Flow Rate: | 1.7 mL/min |
| | Gradient: | A: Water/formic acid |
| | | B: MeCN/formic acid |

| Time | A % | B % |
|---|---|---|
| 0.00 | 95 | 5 |
| 0.50 | 95 | 5 |
| 5.00 | 2 | 98 |
| 6.40 | 2 | 98 |
| 6.50 | 95 | 5 |
| 7.50 | 95 | 5 |

Intermediate 1

(R,E)-N-[(2,8-Dichloroquinolin-3-yl)methylidene]-2-methylpropane-2-sulfinamide

To a solution of 2,8-dichloroquinoline-3-carboxaldehyde (43.0 g, 0.19 mol) in anhydrous THF (500 mL) was added titanium(IV) isopropoxide (114 mL, 0.38 mol) at r.t. After stirring for 15 minutes, (R)-2-methyl-2-propanesulfinamide (23.0 g, 0.19 mol) was added and stirring was continued for 17 h at r.t. Water (1 L) was added to the reaction mixture and the resulting precipitate was filtered and washed with DCM. The organic layer was dried ($Na_2SO_4$) and concentrated in vacuo to give the title compound (61 g, 97%) as a pale yellow solid. $\delta_H$ ($CDCl_3$) 9.11 (1H, s), 8.83 (1H, s), 7.93 (1H, dd, J 7.54, 1.31 Hz), 7.88 (1H, dd, J 8.22, 1.31 Hz), 7.55 (1H, t, J 7.88 Hz), 1.33 (9H, s).

Intermediate 2

(R)-N-[(S)-1-(2,8-Dichloroquinolin-3-yl)ethyl]-2-methylpropane-2-sulfinamide

To a solution of Intermediate 1 (61 g, 0.18 mol) in DCM (1.5 L) was added dropwise methylmagnesium bromide (123.5 mL, 0.37 mol; 3M in $Et_2O$) over 50 minutes at −70° C. under nitrogen. The reaction mixture was allowed to reach r.t. with stirring overnight. The mixture was cooled in an ice-salt bath and saturated aqueous $NH_4Cl$ (500 mL) was slowly added. The aqueous layer was extracted with DCM (2×500 mL). The combined organic layers were dried ($MgSO_4$) and concentrated in vacuo. The residue was triturated with $Et_2O$ and the solid filtered, washed with $Et_2O$ and dried under reduced pressure to give the title compound (32 g, 50%) as a pale pink solid. $\delta_H$ ($CDCl_3$) 8.26 (1H, s), 7.83 (1H, dd, J 7.52, 1.32 Hz), 7.74 (1H, dd, J 8.19, 1.32 Hz), 7.49 (1H, t, J 7.86 Hz), 5.16-5.07 (1H, m), 3.47 (1H, d, J 4.63 Hz), 1.71 (3H, d, J 6.75 Hz), 1.25 (9H, s).

Intermediate 3

(S)-1-(2,8-Dichloroquinolin-3-yl)ethanamine

To a solution of Intermediate 2 (37.7 g, 0.11 mol) in MeOH (370 mL) was added 4M hydrogen chloride in 1,4-dioxane (58 mL) at r.t. The reaction mixture was stirred for 2 h and concentrated in vacuo. The residue was partitioned between 5M HCl (300 mL) and DCM (300 mL). The organic layer was extracted with 5M aqueous HCl (100 mL) and the combined aqueous layers basified with aqueous NaOH and extracted with DCM (3×500 mL) and chloroform (3×500 mL). The organic layers were dried ($MgSO_4$) and concentrated in vacuo to afford the title compound (23.7 g, 90%) as an amber oil. $\delta_H$ ($CDCl_3$) 8.40 (1H, s), 7.80 (1H, dd, J 7.51, 1.33 Hz), 7.75 (1H, dd, J 8.19, 1.33 Hz), 7.46 (1H, t, J 7.86 Hz), 4.67 (1H, q, J 6.52 Hz), 1.50 (3H, d, J 6.53 Hz).

Intermediate 4

(S)-tert-Butyl 1-(2,8-dichloroquinolin-3-yl)ethylcarbamate

To a stirred solution of Intermediate 3 (23.7 g, 98 mmol) and DIPEA (51 mL, 0.3 mol) in DCM (1 L) was added di-tert-butyl dicarbonate (25.7 g, 118 mmol). The reaction mixture was allowed to stand at r.t. overnight and concentrated in vacuo. The residue was triturated with 40-60 petroleum ether, filtered, washed with 40-60 petroleum ether and dried under reduced pressure to give the title compound (28.4 g, 85%) as a colourless solid. $\delta_H$ ($CDCl_3$) 8.13 (1H, s), 7.80 (1H, dd, J 7.51, 1.32 Hz), 7.72 (1H, dd, J 8.18, 1.31 Hz), 7.46 (1H, t, J 7.85 Hz), 5.23-5.16 (1H, m), 5.10 (1H, br s), 1.55 (3H, br d, J 7.18 Hz), 1.42 (9H, br s).

Intermediate 5

(S)-tert-Butyl 1-[8-chloro-2-(3-oxopiperazin-1-yl)quinolin-3-yl]ethylcarbamate

A mixture of Intermediate 4 (0.53 g, 1.56 mmol), 2-oxopiperazine (0.78 g, 7.78 mmol) and DIPEA (1.35 mL, 7.78 mmol) in NMP (10 mL) was heated at 140° C. for 16 h. After cooling, $Et_2O$ (250 mL) was added and the mixture washed with water (3×100 mL) and brine (100 mL). The organic layer was separated, dried ($MgSO_4$), concentrated in vacuo and the residue purified by column chromatography on silica, eluting with 0-100% EtOAc in isohexane, to afford the title compound (0.34 g, 53%) as a pale yellow solid. $\delta_H$ ($CDCl_3$) 8.03 (1H, s), 7.72 (1H, dd, J 7.5, 1.3 Hz), 7.63 (1H, dd, J 8.0, 1.3 Hz), 7.32 (1H, t, J 7.8 Hz), 6.32 (1H, br s), 5.15-4.93 (2H, m), 4.36 (1H, d, J 17.7 Hz), 4.13-3.84 (2H, m), 3.77-3.68 (1H, m), 3.45 (2H, m), 1.48-1.42 (12H, m).

Intermediate 6

(S)-4-[3-(1-Aminoethyl)-8-chloroquinolin-2-yl]piperazin-2-one

TFA (1 mL) was added to a stirred solution of Intermediate 5 (0.34 g, 0.83 mmol) in DCM (5 mL) and the mixture was allowed to stand at r.t. for 16 h before being concentrated in vacuo. The residue was dissolved in DCM (20 mL) and washed with 0.1M NaOH solution. 15% aqueous NaOH solution was added to the aqueous layer which was extracted with EtOAc (20 mL) and DCM (2×20 mL). The combined organics were dried (MgSO$_4$) and concentrated in vacuo to afford the title compound (0.24 g, 95%) as a pale orange-yellow solid. $\delta_H$ (CDCl$_3$) 8.41 (1H, s), 7.73-7.66 (2H, m), 7.38-7.27 (1H, m), 4.81 (1H, m), 4.02 (1H, d, J 17.5 Hz), 3.88 (1H, d, J 17.5 Hz), 3.59-3.38 (4H, m), 2.93 (3H, br s), 1.69 (3H, d, J 6.7 Hz).

Intermediate 7

(E)-N-[(2-Chloro-7-fluoro-8-methylquinolin-3-yl) methylidene]-(R)-2-methylpropane-2-sulfinamide Following the procedure described for Intermediate 1, 2-chloro-7-fluoro-8-methylquinoline-3-carbaldehyde (6.6 g, 29.5 mmol), titanium(IV) isopropoxide (17.0 g, 60 mmol), (R)-2-methyl-2-propanesulfinamide (3.6 g, 29.5 mmol) and THF (200 mL) gave the title compound (8.3 g, 86%) as a yellow solid. $\delta_H$ (CDCl$_3$) 9.12 (1H, s), 8.73 (1H, s), 7.71 (1H, dd, J 6.0 Hz), 7.40 (1H, t, J 8.2 Hz), 2.69 (3H, s), 1.32 (9H, s).

Intermediate 8

N-[(S)-1-(2-Chloro-7-fluoro-8-methylquinolin-3-yl) ethyl]-(R)-2-methylpropane-2-sulfinamide Following the procedure described for Intermediate 2, Intermediate 7 (8.3 g, 25.4 mmol), methylmagnesium bromide (16.0 mL, 48 mmol; 3.0M in Et$_2$O), and DCM (100 mL) gave the title compound (4.2 g, 48%) as a yellow solid. $\delta_H$ (CDCl$_3$) 8.17 (1H, s), 7.63 (1H, dd, J 6.0 Hz), 7.32 (1H, t, J 8.8 Hz), 5.16 (1H, q, J 6.8 Hz), 3.45 (1H, d, J 6.8 Hz), 2.66 (3H, s) 1.70 (3H, d, J 6.8 Hz), 1.26 (9H, s).

Intermediate 9

(S)-tert-Butyl 1-(2-chloro-7-fluoro-8-methylquinolin-3-yl)ethylcarbamate

Following the procedure described for Intermediate 3 followed by Intermediate 4, Intermediate 8 (4.2 g, 12.2 mmol), conc. HCl (1 mL), di-tert-butyl dicarbonate (2.7 g, 12.2 mmol) and DIPEA (1.6 g, 12.2 mmol) gave the title compound (4.38 g, 90%) as a yellow solid. $\delta_H$ (CDCl$_3$) 8.07 (1H, s), 7.62 (1H, dd, J 6.0 Hz), 7.30 (1H, t, J 8.8 Hz), 5.17 (1H, m), 5.07 (1H, br s), 2.65 (3H, s) 1.54 (3H, d, J 6.4 Hz), 1.42 (9H, s).

Intermediate 10

(S)-tert-Butyl 1-[7-fluoro-8-methyl-2-(3-oxopiperazin-1-yl)quinolin-3-yl]ethylcarbamate Following the procedure described for Intermediate 5, Intermediate 9 (280 mg, 0.83 mmol), 2-oxopiperazine (86 mg, 1.0 mmol) and DIPEA (0.5 mL, 3.8 mmol) in n-butanol (2.0 mL) gave the title compound (270 mg, 81%) as a purple oil. $\delta_H$ (CDCl$_3$) 7.99 (1H, s), 7.54 (1H, dd, J 8.9, 6.0 Hz), 7.17 (1H, t, J 9.0 Hz), 6.73 (1H, br s), 5.10 (2H, br s), 4.28 (1H, d, J 17.5 Hz), 3.95 (1H, d, J 17.5 Hz), 3.89-3.77 (1H, m), 3.70-3.51 (1H, m), 3.44-3.35 (2H, m), 2.58 (3H, d, J 2.4 Hz), 1.50-1.30 (12H, m).

Intermediate 11

(S)-4-[3-(1-Aminoethyl)-7-fluoro-8-methylquinolin-2-yl]piperazin-2-one

TFA (10 mL) was added to a stirred solution of Intermediate 10 (1.5 g, 3.73 mmol) in DCM (30 mL) and the mixture was allowed to stand at r.t. for 16 h. Ice was added to this mixture, followed by 2M NaOH solution (alkaline pH). The aqueous layer was separated and washed with DCM. The combined organics were dried (MgSO$_4$) and concentrated in vacuo to afford the title compound (1.1 g, 97%) as a clear oil. $\delta_H$ (CDCl$_3$) 8.16 (1H, s), 7.59-7.51 (1H, m), 7.17 (1H, t, J 9.0 Hz), 6.45 (1H, br s), 4.50 (1H, q, J 6.5 Hz), 4.10 (2H, s), 3.69-3.60 (1H, m), 3.61-3.49 (3H, m), 2.59 (3H, d, J 2.4 Hz), 1.50 (3H, d, J 6.5 Hz).

Intermediate 12

(S)-tert-Butyl 1-[2-(4-acetylpiperazin-1-yl)-7-fluoro-8-methylquinolin-3-yl)]ethylcarbamate Intermediate 9 (3.0 g, 0.89 mmol) in NMP (15 mL) was treated with 1-acetylpiperazine (2.8 g, 22 mmol) and DIPEA (5.7 g, 44 mmol) and heated in a sealed tube at 140° C. for 72 h. The reaction mixture was cooled to r.t. and diluted with ethyl acetate/water. The organic phase was washed (water, brine), dried (phase separation cartridge) and evaporated in vacuo. The resulting residue was purified by silica flash chromatography, eluting with 50-60% EtOAc in isohexane, to give the title compound (3.4 g 89%) as a cream solid. $\delta_H$ (CDCl$_3$) 7.95 (1H, s), 7.53 (1H, dd, J 8.9, 6.0 Hz), 7.16 (1H, t, J 8.9 Hz), 5.08-5.02 (1H, m), 3.95-3.90 (1H, m), 3.78-3.73 (2H, m), 3.64 (1H, m), 3.61-3.40 (2H, m), 3.19-3.15 (2H, m), 2.59 (3H, d, J 2.4 Hz), 2.17 (3H, s), 1.58 (3H, d, J=6.5 Hz), 1.48-1.42 (9H, m).

Intermediate 13

(S)-1-{4-[3-(1-Aminoethyl)-7-fluoro-8-methylquinolin-2-yl]piperazin-1-yl}ethanone Intermediate 12 (3.4 g, 7.9 mmol) in DCM (20 mL) was treated with TFA (10 mL) and stirred for 30 minutes. The reaction mixture was evaporated in vacuo. The residue was dissolved in MeOH and passed through an SCX cartridge, washing with MeOH and eluting with 7M NH$_3$/MeOH solution. After evaporation in vacuo, the title compound (2.6 g, 100%) was obtained as a white foam. $\delta_H$ (CDCl$_3$) 8.12 (1H, s), 7.54 (1H, dd, J 8.9, 6.1 Hz), 7.16 (1H, t, J 8.9 Hz), 4.53 (1H, q, J 6.5 Hz), 3.82 (2H, t, J 5.0 Hz), 3.72-3.64 (2H, m), 3.41-3.20 (4H, m), 2.59 (3H, d, J 2.4 Hz), 2.17 (3H, s), 2.07 (2H, br s), 1.51 (3H, d, J 6.5 Hz).

Intermediate 14

(S)-tert-Butyl 1-{7-fluoro-8-methyl-2-[4-(pyridin-2-yl)piperazin-1-yl]quinolin-3-yl}ethylcarbamate Intermediate 9 (500 mg, 1.5 mmol) in NMP (6 mL) was treated with 1-(pyridin-2-yl)piperazine (482 mg, 3 mmol) and DIPEA (1.3 mL, 7.5 mmol) and heated in a sealed tube at 140° C. for 24 h. The reaction mixture was cooled to r.t. and diluted with EtOAc/water. The organic phase was washed with water and brine, dried (phase separation cartridge) and evaporated in vacuo. The resulting residue was purified by flash chromatography on silica, eluting with 10-20% EtOAc in isohexane, to give the title compound (530 mg, 76%) as a solid. $\delta_H$ (CDCl$_3$) 8.23 (1H, dd, J 4.9, 1.9 Hz), 7.94 (1H, s), 7.54-7.48 (2H, m), 7.15 (1H, t, J 8.9 Hz), 6.73 (1H, d, J 8.6 Hz), 6.65 (1H, t, J 5.9 Hz), 5.23-5.20 (1H, m) 5.10-4.91 (1H, m), 3.86-3.84 (2H, m), 3.76-3.63 (4H, m), 3.35-3.27 (2H, m), 2.60 (3H, d, J 2.4 Hz), 1.48-1.41 (12H, m).

Intermediate 15

(S)-tert-Butyl 1-{7-fluoro-8-methyl-2-[4-(pyrazin-2-yl)piperazin-1-yl]quinolin-3-yl}ethylcarbamate Following the procedure described for Intermediate 14, Intermediate 9 (500 mg, 1.5 mmol), 2-(piperazin-1-yl)pyrazine (485 mg, 3.0 mmol) and DIPEA (1.3 mL, 7.5 mmol) in NMP (6 mL) gave the title compound (470 mg, 68%) as a solid. $\delta_H$ (CDCl$_3$) 8.22 (1H, s), 8.10 (1H, t, J 1.9 Hz), 7.96 (1H, s), 7.88 (1H, d, J 2.6 Hz), 7.53 (1H, dd, J 8.9, 6.0 Hz), 7.16 (1H, t, J 8.9 Hz), 5.18 (1H, br s), 4.99 (1H, br s), 3.93-3.83 (2H, m), 3.81-3.73 (2H, m), 3.72-3.64 (2H, m), 3.34-3.27 (2H, m), 2.60 (3H, d, J 2.4 Hz), 1.49-1.42 (12H, m).

Intermediate 16

(S)-tert-Butyl 1-[7-fluoro-8-methyl-2-(4-propionylpiperazin-1-yl)quinolin-3-yl]ethylcarbamate Following the procedure described for Intermediate 14, Intermediate 9 (500 mg, 1.5 mmol), 1-(piperazin-1-yl)propan-1-one (420 mg, 3.0 mmol) and DIPEA (1.3 mL, 7.5 mmol) in NMP (6 mL) gave the title compound (470 mg, 71%) as a solid. $\delta_H$ (CDCl$_3$) 7.94 (1H, s), 7.52 (1H, dd, J 8.8, 6.1 Hz), 7.16 (1H, t, J 8.9 Hz), 5.14 (1H, br s), 4.96 (1H, br s), 3.95-3.73 (2H, m), 3.71-3.58 (1H, m), 3.62-3.48 (3H, m), 3.22-3.08 (2H, s), 2.59 (3H, d, J 2.4 Hz), 2.42 (2H, q, J 7.4 Hz), 1.48-1.42 (12H, m), 1.28-1.14 (3H, m).

Intermediate 17

(S)-1-{4-[3-(1-Aminoethyl)-7-fluoro-8-methylquinolin-2-yl]piperazin-1-yl}propan-1-one Following the procedure described for Intermediate 13, Intermediate 16 (470 mg, 1.1 mmol) and TFA (3 mL) in DCM (6 mL) afforded the title compound (364 mg, 99%) as a white foam, which was used in the next step without any further purification. $\delta_H$ (CDCl$_3$) 8.11 (1H, s), 7.54 (1H, dd, J 8.9, 6.1 Hz), 7.15 (1H, t, J 9.0 Hz), 4.51 (1H, q, J 6.5 Hz), 3.84 (2H, t, J 5.1 Hz), 3.69 (2H, t, J 5.2 Hz), 3.43-3.21 (4H, m), 2.59 (3H, d, J 2.4 Hz), 2.43 (2H, q, J 7.5 Hz), 1.63 (2H, br s+H$_2$O), 1.50 (3H, d, J 6.5 Hz), 1.20 (3H, t, J 7.5 Hz).

Intermediate 18

(S)-tert-Butyl 1-[7-fluoro-8-methyl-2-(4-pivaloylpiperazin-1-yl)quinolin-3-yl]ethylcarbamate Following the procedure described for Intermediate 14, Intermediate 9 (500 mg, 1.5 mmol), 2,2-dimethyl-1-(piperazin-1-yl)propan-1-one (500 mg, 3 mmol) and DIPEA (1.3 mL, 7.5 mmol) in NMP (6 mL) gave the title compound (460 mg, 65%) as a solid. $\delta_H$ (CDCl$_3$) 7.94 (1H, s), 7.52 (1H, dd, J 8.8, 6.1 Hz), 7.16 (1H, t, J 8.9 Hz), 5.14 (1H, s), 4.96 (1H, s), 3.93 (2H, d, J 11.7 Hz), 3.82 (2H, t, J 8.7 Hz), 3.52 (2H, t, J 8.9 Hz), 3.15 (2H, m), 2.59 (3H, d, J 2.4 Hz), 1.48-1.41 (12H, m), 1.34 (9H, s).

Intermediate 19

(S)-1-{4-[3-(1-Aminoethyl)-7-fluoro-8-methylquinolin-2-yl]piperazin-1-yl}-2,2-dimethylpropan-1-one Following the procedure described for Intermediate 13, Intermediate 18 (460 mg, 0.97 mmol) and TFA (3 mL) in DCM (6 mL) afforded the title compound (358 mg, 99%) as a white foam, which was used in the next step without any further purification. $\delta_H$ (CDCl$_3$) 8.11 (1H, s), 7.54 (1H, dd, J 8.8, 6.1 Hz), 7.15 (1H, t, J 9.0 Hz), 4.51 (1H, q, J 6.5 Hz), 3.89-3.83 (4H, m), 3.39-3.26 (4H, m), 2.60 (3H, d, J 2.4 Hz), 1.62 (2H, br s+H$_2$O), 1.50 (3H, d, J 6.5 Hz), 1.34 (9H, s).

Intermediate 20

(S)-Methyl 4-{3-[1-(tert-butoxycarbonylamino)ethyl]-7-fluoro-8-methylquinolin-2-yl}piperazine-1-carboxylate A solution of Intermediate 9 (501 mg, 1.49 mmol), methyl piperazine-1-carboxylate (981 mg, 6.80 mmol) and DIPEA (1.29 mL, 7.39 mmol) in NMP (3 mL) was heated to 130° C. under microwave irradiation for 4.5 h. After cooling, the reaction mixture was dissolved in a 1:1 mixture of EtOAc and Et$_2$O (250 mL) and washed with saturated brine (3×50 mL). The organic layer was dried (MgSO$_4$) and concentrated in vacuo. Purification by column chromatography on silica, eluting with 10% EtOAc in DCM, gave the title compound (400 mg, 60%) as a pale yellow oil. $\delta_H$ (CDCl$_3$) 7.94 (1H, s), 7.52 (1H, dd, J 8.8, 6.1 Hz), 7.15 (1H, t, J 8.9 Hz), 5.12 (1H, br s), 4.95 (1H, br s), 3.82-3.68 (5H, m), 3.65 (2H, m), 3.49 (2H, m), 3.14 (2H, m), 2.59 (3H, d, J 2.40 Hz), 1.47-1.41 (12H, m). LCMS (ES+) 447 (M+H)$^+$.

Intermediate 21

(S)-tert-Butyl 1-[2-(4-acetylpiperazin-1-yl)-8-chloroquinolin-3-yl]ethylcarbamate Following the procedure described for Intermediate 5, Intermediate 4 (300 mg, 0.88 mmol), 1-acetylpiperazine (564 mg, 4.40 mmol), NMP (3 mL) and DIPEA (1.53 mL, 8.80 mmol) gave the title compound (0.25 mg, 65%) as a clear glass. $\delta_H$ (CDCl$_3$) 8.01 (1H, s), 7.71 (1H, dd, J 7.5, 1.4 Hz), 7.62 (1H, dd, J 8.0, 1.4 Hz), 7.31 (1H, t, J 7.8 Hz), 5.08 (1H, m), 3.94-3.71 (3H, m), 3.67-3.52 (3H, m), 3.39-3.15 (2H, m), 2.16 (3H, s), 1.76 (1H, d, J 2.5 Hz), 1.48-1.43 (12H, m).

Intermediate 22

(S)-4-[3-(1-Aminoethyl)-7-fluoro-8-methylquinolin-2-yl]piperazine-1-carboxamide

A solution of Intermediate 9 (2 g, 5.9 mmol), piperazine (2.6 g, 30.2 mmol) and DIPEA (5.1 mL, 29.4 mmol) in NMP (12 mL) was heated at 140° C. for 16 h. After cooling, the mixture was dissolved in EtOAc (150 mL) and washed with water (2×50 mL) and saturated brine (50 mL). The organic layer was dried using a phase separation cartridge and concentrated in vacuo to give a white foam (2.29 g, 100%). LCMS (ES+) 389 (M+H)$^+$. To a solution of this foam (400 mg, 1.03 mmol) and Et$_3$N (0.43 mL, 3.09 mmol) in DCM (5 mL) was added trimethylsilyl isocyanate (154 mg, 1.34 mmol). The reaction mixture was stirred at r.t. for 17 h and the excess solvent was removed in vacuo. Purification by column chromatography (SiO$_2$, 95:4:1 DCM/MeOH/NH$_3$ solution in MeOH) gave a colourless glass (419 mg, 94%). LCMS (ES+) 432 (M+H)$^+$. To this glass (402 mg, 0.932 mmol) dissolved in DCM (24 mL) was added TFA (4.2 mL). The reaction mixture was stirred at r.t. for 1.5 h. Excess solvent was removed in vacuo. The oil obtained was basified with 0.2M NaOH solution (40 mL) and extracted with EtOAc (3×80 mL). The combined organic layers were dried (MgSO$_4$), filtered and concentrated in vacuo to give the title compound (349 mg, 100%) as a white foam. $\delta_H$ (DMSO-$d_6$) 8.39 (1H, s), 7.75 (1H, dd, J 8.92, 6.37 Hz), 7.31 (1H, t, J 9.14 Hz), 6.08 (2H, s), 4.39-4.34 (1H, m), 3.46-3.59 (5H, m), 3.35 (2H, m, masked by water peak), 3.12-3.19 (3H, m), 2.55 (3H, d, J 2.40 Hz), 1.39 (3H, d, J 6.42 Hz).

Example 1

(S)-4-{8-Chloro-3-[1-(pyrido[3,2-d]pyrimidin-4-ylamino)ethyl]quinolin-2-yl}piperazin-2-one A solution/suspension of Intermediate 6 (100 mg, 0.33 mmol), 4-chloropyrido[3,2-d]pyrimidine (18 mg, 0.14 mmol) and DIPEA (0.17 mL, 0.98 mmol) in NMP (2 mL) was heated at 140° C. overnight. The solvent was removed in vacuo and the residue purified by preparative HPLC to afford the title compound (48 mg, 33%) as a light brown solid. $\delta_H$ (CDCl$_3$) 8.77 (1H, dd, J 4.3, 1.6 Hz), 8.57 (1H, s), 8.15-8.12 (2H, m), 7.74-7.70 (2H, m), 7.60-7.57 (2H, m), 7.30 (1H, t, J 7.8 Hz), 6.00 (1H, s), 5.80-5.72 (1H, m), 4.49-4.45 (1H, m), 4.20-4.12 (2H, m), 3.90-3.82 (1H, m), 3.57-3.48 (2H, m), 1.69 (3H, d, J 6.7 Hz). LCMS (ES+) 434 (M+H)$^+$, RT 2.25 minutes (Method 2).

Example 2

(S)-2-(4-{8-Chloro-3-[1-(pyrido[3,2-d]pyrimidin-4-ylamino)ethyl]quinolin-2-yl}piperazin-1-yl)ethanol Intermediate 4 (0.7 g, 2.05 mmol), 2-(piperazin-1-yl)ethanol (1 mL, 8.15 mmol), n-butanol (6 mL) and DIPEA (1 mL, 5.74 mmol) were combined in a sealed tube and heated to 120-130° C. for 7 days. Reaction progression was followed by LCMS. Upon completion, the mixture was evaporated to dryness on silica and purified by flash chromatography. The resulting product was treated at r.t. with MeOH (5 mL) and 2M HCl in diethyl ether (5 mL). When LCMS analysis of the reaction mixture indicated complete conversion of the starting material, the mixture was evaporated to dryness. The resulting amine intermediate (HCl salt, 50 mg) was combined with 4-chloropyrido[3,2-d]pyrimidine (50 mg) in n-butanol (5 mL) and DIPEA (1 mL). The reaction mixture was heated in a sealed tube under microwave irradiation to 140° C. for 1 h. When LCMS analysis of the reaction mixture indicated completion, the mixture was evaporated to dryness and purified by preparative HPLC to give the title compound (47 mg) as an off-white solid. $\delta_H$ (DMSO-$d_6$) 8.93-8.88 (2H, m), 8.52 (2H, d, J 4.7 Hz), 8.18 (1H, dd, J 8.5, 1.6 Hz), 7.91 (1H, m), 7.80 (2H, t, J 7.2 Hz), 7.39 (1H, t, J 7.8 Hz), 5.91-5.83 (1H, m), 4.45 (1H, t, J 5.35 Hz), 3.70 (3H, m), 3.59 (2H, q, J 5.6 Hz), 3.21 (3H, m), 2.78-2.72 (2H, m), 2.70-2.61 (3H, m), 1.66 (3H, d, J 6.7 Hz). LCMS (ES+) 464 (M+H)$^+$, RT 7.09 minutes (Method 3).

Example 3

(S)-4-{7-Fluoro-8-methyl-3-[1-(pyrido[2,3-d]pyrimidin-4-ylamino)ethyl]quinolin-2-yl}piperazin-2-one A solution/suspension of Intermediate 11 (110 mg, 0.36 mmol), 4-chloropyrido[2,3-d]pyrimidine (83 mg, 0.54 mmol) and DIPEA (0.19 mL, 1.08 mmol) in n-butanol (2.9 mL) was heated at 140° C. overnight. The solvent was removed in vacuo and the residue purified by preparative HPLC to afford the title compound (80 mg, 52%) as a solid. $\delta_H$ (CDCl$_3$) 9.03 (1H, dd, J 4.4, 1.8 Hz), 8.71 (1H, s), 8.44 (1H, dd, J 8.22, 1.86 Hz), 8.07 (1H, s), 7.46-7.37 (2H, m), 7.12 (1H, t, J 8.9 Hz), 6.39 (1H, br s), 5.82 (1H, q, J 6.7 Hz), 4.33 (1H, d, J 17.4 Hz), 4.05-3.94 (2H, m), 3.65 (1H, m), 3.60-3.51 (1H, m), 3.46-3.39 (1H, m), 2.62-2.56 (3H, m), 1.66 (3H, d, J 6.69 Hz), NH missing. LCMS (ES+) 432 (M+H)$^+$, RT 7.46 minutes (Method 3).

Example 4

(S)-4-{7-Fluoro-8-methyl-3-[1-(pyrido[3,2-d]pyrimidin-4-ylamino)ethyl]quinolin-2-yl}piperazin-2-one Following the procedure described for Example 3, Intermediate 11 (110 mg, 0.36 mmol), 4-chloropyrido[3,2-d]pyrimidine (83 mg, 0.54 mmol) and DIPEA (0.19 mL, 1.08 mmol) in n-butanol (2.9 mL) gave the title compound (72 mg, 46%) as a solid. $\delta_H$ (CDCl$_3$) 8.76 (1H, dd, J 4.3, 1.6 Hz), 8.57 (1H, s), 8.14 (1H, dd, J 8.5, 1.6 Hz), 8.11 (1H, s), 7.71 (1H, dd, J 8.5, 4.3 Hz), 7.63 (1H, d, J 7.4 Hz), 7.51 (1H, dd, J 8.9, 6.0 Hz), 7.16 (1H, t, J 8.9 Hz), 6.41 (1H, br s), 5.82-5.73 (1H, m), 4.38 (1H, d, J 17.4 Hz), 4.09-3.98 (2H, m), 3.74-3.67 (1H, m), 3.59-3.41 (2H, m), 2.60 (3H, d, J 2.4 Hz), 1.69 (3H, d, J 6.7 Hz). LCMS (ES+) 432 (M+H)$^+$, RT 7.71 minutes (Method 3).

Example 5

(S)-1-(4-{7-Fluoro-8-methyl-3-[1-(pyrido[3,2-d]pyrimidin-4-ylamino)ethyl]quinolin-2-yl}piperazin-1-yl)ethanone Intermediate 13 (0.07 g, 0.21 mmol), 4-chloropyrido[3,2-d]pyrimidine (42 mg, 0.25 mmol) and DIPEA (0.141 g, 1.1 mmol) in NMP (1.5 mL) were heated under microwave conditions at 150° C. for 1 h. Purification by preparative HPLC afforded the title compound (34 mg, 35%) as an off-white solid. $\delta_H$ (DMSO-$d_6$) 8.93-8.88 (2H, m), 8.54 (2H, d, J 12.0 Hz), 8.17 (1H, dd, J 8.4, 1.6 Hz), 7.90 (1H, dd, J 8.5, 4.3 Hz), 7.74 (1H, dd, J 8.9, 6.3 Hz), 7.33 (1H, t, J 9.2 Hz), 5.90 (1H, t, J 7.2 Hz), 3.78 (2H, t, J 7.4 Hz), 3.71-3.56 (4H, m), 3.24-3.05 (2H, m), 2.57 (3H, d, J 2.3 Hz), 2.11 (3H, s), 1.66 (3H, d, J 6.7 Hz). LCMS (ES+) 460 (M+H)$^+$, RT 2.6 minutes (Method 2).

Example 6

(S)-1-(4-{7-Fluoro-8-methyl-3-[1-(1,5-naphthyridin-4-ylamino)ethyl]quinolin-2-yl}piperazin-1-yl)ethanone Following the procedure described for Example 5, Intermediate 13 (70 mg, 0.21 mmol), 4-chloro-1,5-naphthyridine (42 mg, 0.25 mmol) and DIPEA (0.18 mL, 1.1 mmol) in NMP (1.2 mL) afforded the title compound (7 mg, 7%) as an off-white solid. $\delta_H$ (DMSO-$d_6$) 8.83 (1H, d, J 4.1 Hz), 8.62 (1H, s), 8.43 (1H, d, J 5.3 Hz), 8.24 (1H, s), 8.19 (1H, d, J 8.5 Hz), 7.73 (2H, dd, J 8.3, 4.7 Hz), 7.31 (1H, t, J 9.1 Hz), 6.77 (1H, d, J 5.3 Hz), 5.11 (1H, m), 3.89-3.71 (4H, m), 3.43-3.19 (4H, m), 2.56 (3H, s), 2.13 (3H, s), 1.86 (3H, d, J 6.6 Hz). LCMS (ES+) 459 (M+H)$^+$, RT 2.4 minutes (Method 2).

Example 7

(S)-N-(1-{7-Fluoro-8-methyl-2-[4-(pyridin-2-yl)piperazin-1-yl]quinolin-3-yl}ethyl)pyrido[3,2-d]pyrimidin-4-amine Following the procedure described for Intermediate 13, Intermediate 14 (530 mg, 1.1 mmol) and TFA (3 mL) in DCM (6 mL) afforded (S)-1-{7-fluoro-8-methyl-2-[4-(pyridin-2-yl)piperazin-1-yl]quinolin-3-yl}ethanamine as a white foam, which was used in the next step without any further purification. Following the procedure described for Example 5, (S)-1-{7-fluoro-8-methyl-2-[4-(pyridin-2-yl)piperazin-1-yl]quinolin-3-yl}ethanamine (60 mg, 0.16 mmol), 4-chloropyrido[3,2-d]pyrimidine (33 mg, 0.19 mmol) and DIPEA (0.14 mL, 0.8 mmol) in NMP (1.2 mL) afforded the title compound (46 mg, 58%) as a beige solid. $\delta_H$ (DMSO-d$_6$) 8.94-8.89 (2H, m), 8.56 (1H, s), 8.52 (1H, s), 8.20-8.16 (2H, m), 7.91 (1H, dd, J 8.5, 4.3 Hz), 7.74 (1H, dd, J 8.9, 6.3 Hz), 7.65-7.55 (1H, m), 7.32 (1H, t, J 9.1 Hz), 6.96 (1H, d, J 8.6 Hz), 6.71 (1H, dd, J 7.1, 4.9 Hz), 5.95 (1H, m), 3.87-3.69 (6H, m), 3.33-3.23 (2H, m), 2.58 (3H, s), 1.68 (3H, d, J 6.7 Hz). LCMS (ES+) 495 (M+H)$^+$, RT 3.09 minutes (Method 4).

Example 8

(S)-N-(1-{7-Fluoro-8-methyl-2-[4-(pyrazin-2-yl)piperazin-1-yl]quinolin-3-yl}ethyl)pyrido[3,2-d]pyrimidin-4-amine Following the procedure described for Intermediate 13, Intermediate 15 (470 mg, 1.1 mmol) and TFA (3 mL) in DCM (6 mL) afforded (S)-1-{7-fluoro-8-methyl-2-[4-(pyrazin-2-yl)piperazin-1-yl]quinolin-3-yl}ethanamine as a white foam, which was used in the next step without any further purification. Following the procedure described for Example 5, (S)-1-{7-fluoro-8-methyl-2-[4-(pyrazin-2-yl)piperazin-1-yl]quinolin-3-yl}-ethanamine (60 mg, 0.16 mmol), 4-chloropyrido[3,2-d]pyrimidine (33 mg, 0.19 mmol) and DIPEA (0.14 mL, 0.8 mmol) in NMP (1.2 mL) afforded the title compound (37 mg, 46%) as a brown solid. $\delta_H$ (DMSO-d$_6$) 8.95-8.89 (2H, m), 8.55 (2H, d, J 14.1 Hz), 8.45 (1H, d, J 1.5 Hz), 8.19-8.14 (2H, m), 7.93-7.88 (2H, m), 7.74 (1H, dd, J 8.9, 6.3 Hz), 7.33 (1H, t, J 9.1 Hz), 5.98-5.90 (1H, m), 3.96-3.87 (2H, m), 3.87-3.75 (4H, m), 3.33-3.25 (2H, m), 2.58 (3H, d, J 2.3 Hz), 1.68 (3H, d, J 6.7 Hz). LCMS (ES+) 496 (M+H)$^+$, RT 4.07 minutes (Method 4).

Example 9

(S)-1-(4-{7-Fluoro-8-methyl-3-[1-(pyrido[3,2-d]pyrimidin-4-ylamino)ethyl]quinolin-2-yl}piperazin-1-yl)propan-1-one Following the procedure described for Example 5, Intermediate 17 (60 mg, 0.16 mmol), 4-chloropyrido[3,2-d]pyrimidine (33 mg, 0.19 mmol) and DIPEA (0.14 mL, 0.8 mmol) in NMP (1.2 mL) afforded the title compound (56 mg, 74%) as an off white solid. $\delta_H$ (DMSO-d$_6$) 8.64 (1H, s), 8.42 (1H, d, J 7.8 Hz), 8.13 (1H, t, J 2.2 Hz), 7.74 (1H, dd, J 8.9, 6.2 Hz), 7.33 (1H, t, J 9.1 Hz), 6.44 (1H, d, J 2.3 Hz), 6.28 (1H, d, J 5.3 Hz), 5.22-5.15 (1H, m), 3.87-3.71 (4H, m), 3.25-3.17 (2H, m), 2.56 (3H, d, J 2.3 Hz), 2.45 (2H, q, J 7.4 Hz), 1.89 (3H, d, J 6.7 Hz), 1.08 (3H, t, J 7.4 Hz). LCMS (ES+) 474 (M+H)$^+$, RT 3.64 minutes (Method 4).

Example 10

(S)-1-(4-{7-Fluoro-8-methyl-3-[1-(pyrido[3,2-d]pyrimidin-4-ylamino)ethyl]quinolin-2-yl}piperazin-1-yl)-2,2-dimethylpropan-1-one Following the procedure described for Example 5, Intermediate 19 (60 mg, 0.16 mmol), 4-chloropyrido[3,2-d]pyrimidine (33 mg, 0.19 mmol) and DIPEA (0.14 mL, 0.8 mmol) in NMP (1.2 mL) afforded the title compound (43 mg, 54%) as a brown solid. $\delta_H$ (DMSO-d$_6$) 8.90 (2H, dd, J 5.7, 1.4 Hz), 8.54 (2H, d, J 14.7 Hz), 8.17 (1H, dd, J 8.4, 1.6 Hz), 7.90 (1H, dd, J 8.5, 4.3 Hz), 7.74 (1H, dd, J 8.9, 6.3 Hz), 7.33 (1H, t, J 9.1 Hz), 5.98-5.88 (1H, m), 3.92-3.75 (4H, m), 3.67-3.59 (2H, m), 3.16 (2H, t, J 8.5 Hz), 2.57 (3H, d, J 2.3 Hz), 1.67 (3H, d, J 6.7 Hz), 1.29 (9H, s). LCMS (ES+) 502 (M+H)$^+$, RT 3.04 minutes (Method 2).

Example 11

(S)-Methyl 4-{7-fluoro-8-methyl-3-[1-(pyrido[2,3-d]pyrimidin-4-ylamino)ethyl]quinolin-2-yl}piperazine-1-carboxylate Intermediate 20 (400 mg, 0.89 mmol) was dissolved in DCM (23 mL) and TFA (4.1 mL) was added. The mixture was stirred at r.t. for 1.5 h and excess DCM and TFA were removed in vacuo. The yellow residue obtained was basified using 0.2M aqueous NaOH (40 mL) and extracted with EtOAc (3×80 mL). The combined organic layers were dried (MgSO$_4$) and concentrated in vacuo. Purification by column chromatography on silica, eluting with DCM/MeOH/NH$_3$ (95:4:1), gave a colourless gum (278 mg, 90%). $\delta_H$ (CDCl$_3$) 7.94 (1H, s), 7.52 (1H, dd, J 8.8, 6.1 Hz), 7.15 (1H, t, J 8.9 Hz), 5.11 (1H, br s), 4.98 (1H, br s), 3.80-3.76 (2H, m), 3.75 (3H, s), 3.70-3.59 (2H, m), 3.56-3.42 (2H, m), 3.21-3.07 (2H, m), 2.59 (3H, d, J 2.40 Hz), 1.54 (3H, s). LCMS (ES+) 347 (M+H)$^+$. A solution of this gum (55.6 mg, 0.161 mmol), 4-chloropyrido[2,3-d]pyrimidine (40 mg, 0.24 mmol) and DIPEA (0.084 mL, 0.48 mmol) in n-butanol (1 mL) was heated to 130° C. under microwave irradiation for 1 h. Purification by preparative HPLC afforded the title compound (41 mg, 54%) as a white solid. $\delta_H$ (DMSO-d$_6$) 9.05 (1H, dd, J 4.4, 1.8 Hz), 9.01 (1H, dd, J 8.3, 1.9 Hz), 8.88 (1H, d, J 6.9 Hz), 8.64 (1H, s), 8.36 (1H, s), 7.78 (1H, dd, J 8.9, 6.3 Hz), 7.63 (1H, dd, J 8.2, 4.4 Hz), 7.33 (1H, t, J 9.1 Hz), 5.88-5.78 (1H, m), 3.79-3.57 (6H, m), 3.61-3.51 (3H, m), 3.21-3.09 (2H, m), 2.57 (3H, d, J 2.3 Hz), 1.62 (3H, d, J 6.7 Hz). LCMS (ES+) 478 (M+H)$^+$, RT 7.2 minutes (Method 3).

Example 12

N-[(R)-1-{8-Chloro-3-[(S)-1-(pyrido[3,2-d]pyrimidin-4-ylamino)ethyl]quinolin-2-yl}pyrrolidin-3-yl]-2-hydroxyacetamide (R)-(+)-tert-Butyl 3-aminopyrrolidine-1-carboxylate (400 mg, 2.15 mmol), DCM (30 mL), DIPEA (2 mL) and acetoxyacetyl chloride (0.25 mL, 2.3 mmol) were combined at r.t. and stirred for 6 days. The mixture was diluted with DCM (100 mL), washed with water, dried (MgSO$_4$) and evaporated in vacuo to give a tan oil (747 mg). The crude product was combined with MeOH (10 mL) and 2M HCl in diethyl ether (4 mL) and stirred at r.t. for 19 h. The reaction mixture was then evaporated in vacuo to give a brown gum (528 mg). The resulting residue, Intermediate 4 (400 mg, 1.17 mmol), n-butanol (14 mL) and DIPEA (2 mL) were combined in a sealed tube and heated to 130° C. for 13 days. The reaction mixture was evaporated onto silica and purified by flash chromatography to give an off-white foam (325 mg). The product was combined with MeOH (10 mL) and 2M HCl in diethyl ether (6 mL) and stirred at r.t. for 19 h. The mixture was evaporated to give a yellow solid (326 mg). The resulting amine intermediate (HCl salt, 50 mg) was combined with 4-chloropyrido[3,2-d]pyrimidine (50 mg) in n-butanol (5 mL) and DIPEA (1 mL) and heated in a sealed tube under microwave irradiation to 160° C. for 2 h. The mixture was evaporated to dryness and purified by preparative HPLC to give the title compound (27 mg) as a yellow solid. $\delta_H$ (DMSO-$d_6$) 8.96-8.88 (2H, m), 8.54 (2H, d, J 3.8 Hz), 8.17 (1H, dd, J 8.5, 1.6 Hz), 7.90 (1H, dd, J 8.5, 4.3 Hz), 7.85-7.77 (2H, m), 7.40 (1H, t, J 7.8 Hz), 5.90-5.82 (1H, m), 3.81-3.68 (2H, m), 3.40-3.13 (4H, m), 2.99-2.89 (2H, m), 2.87-2.79 (2H, m), 1.65 (3H, d, J 6.7 Hz). LCMS (ES+) 478 (M+H)$^+$, RT 2.28 minutes (Method 2).

Example 13

N-[(S)-1-{7-Fluoro-8-methyl-3-[(S)-1-(pyrido[3,2-d]pyrimidin-4-ylamino)ethyl]quinolin-2-yl}pyrrolidin-3-yl]cyclopropanecarboxamide (S)-(−)-tert-Butyl 3-aminopyrrolidine-1-carboxylate (500 mg, 2.68 mmol), DCM (30 mL), DIPEA (2 mL) and cyclopropanecarbonyl chloride (0.28 mL, 3.0 mmol) were combined at r.t. and stirred for 2 days. The reaction was diluted with DCM (100 mL), washed with water, dried (MgSO$_4$) and evaporated in vacuo to give a brown oil (866 mg). The crude product was combined with MeOH (10 mL) and 2M HCl in Et$_2$O (5 mL) and stirred at r.t. for 3 days. The reaction mixture was then evaporated in vacuo to give a brown gum (746 mg). The crude compound, Intermediate 9 (500 mg, 1.48 mmol), n-butanol (16 mL) and DIPEA (2 mL) were combined in a sealed tube and heated to 130° C. for 15 days. The reaction mixture was evaporated onto silica and purified by flash chromatography on silica, eluting with 0-100% EtOAc in isohexane, to give a tan solid (779 mg). The product was combined with MeOH (10 mL) and 2N HCl in Et$_2$O (7 mL) and stirred at r.t for 19 h. The reaction mixture was then evaporated in vacuo to give a brown glass (689 mg). The resulting amine intermediate (HCl salt, 50 mg) was combined with 4-chloropyrido[3,2-d]pyrimidine (50 mg) in n-butanol (5 mL) and DIPEA (1 mL). The reaction mixture was heated in a sealed tube under microwave irradiation to 160° C. for 2 h. The mixture was evaporated to dryness and purified by preparative HPLC to give the title compound (32 mg) as a brown glass. $\delta_H$ (DMSO-$d_6$) 8.94-8.90 (2H, m), 8.52 (1H, s), 8.42 (1H, d, J 6.4 Hz), 8.28-8.22 (1H, m), 8.17 (1H, dd, J 8.5, 1.6 Hz), 7.91 (1H, dd, J 8.5, 4.2 Hz), 7.56 (1H, dd, J 8.8, 6.4 Hz), 7.08 (1H, t, J 9.1 Hz), 6.00 (1H, t, J 7.2 Hz), 4.47-4.39 (1H, m), 4.02 (1H, dd, J 10.4, 6.8 Hz), 3.97-3.86 (2H, m), 3.70 (1H, dd, J 10.4, 6.9 Hz), 2.50 (3H, d, J 2.2 Hz), 2.32-2.22 (1H, m), 2.00-1.91 (1H, m), 1.65-1.55 (4H, m), 0.75-0.66 (4H, m). LCMS (ES+) 486 (M+H)$^+$, RT 8.15 minutes (Method 3).

Example 14

(S)-2-(4-{8-Chloro-3-[1-(pyrido[3,2-d]pyrimidin-4-ylamino)ethyl]quinolin-2-yl}piperazin-1-yl)acetic acid Intermediate 4 (700 mg, 2.05 mmol), 2-(piperazin-1-yl)acetic acid ethyl ester (350 mg, 2.05 mmol), DME (10 mL) and DIPEA (1 mL) were combined in a sealed tube and heated to 120° C. for 14 days. The reaction mixture was evaporated onto silica and purified by flash chromatography on silica, eluting with 0-100% EtOAc in isohexane, to give a clear gum (504 mg). The product was combined with EtOH (5 mL) and 2M HCl in diethyl ether (5 mL) and stirred at r.t. for 19 h. A further portion of 2M HCl in diethyl ether (5 mL) was added and stirring continued for a further 3 days. The reaction mixture was then evaporated in vacuo to give a yellow glass (533 mg). The resulting amine intermediate (HCl salt, 60 mg) was combined with 4-chloropyrido[3,2-d]pyrimidine (50 mg) in n-butanol (6 mL) and DIPEA (1 mL). The reaction mixture was heated in a sealed tube under microwave irradiation to 160° C. for 1.5 h. The reaction mixture was treated with a solution of 15% aqueous NaOH (0.4 mL) and stirred at r.t. for 22 h. The mixture was evaporated to dryness and purified by preparative HPLC to give the title compound (35 mg) as a yellow solid. $\delta_H$ (DMSO-$d_6$) 8.96-8.88 (2H, m), 8.54 (2H, d, J 3.8 Hz), 8.17 (1H, dd, J 8.5, 1.6 Hz), 7.90 (1H, dd, J 8.5, 4.3 Hz), 7.85-7.77 (2H, m), 7.40 (1H, t, J 7.8 Hz), 5.90-5.82 (1H, m), 3.78-3.70 (2H, m), 3.40-3.13 (4H, m), 2.97-2.90 (2H, m), 2.88-2.80 (2H, m), 1.65 (3H, d, J 6.7 Hz). LCMS (ES+) 478 (M+H)$^+$, RT 7.2 minutes (Method 3).

Example 15

1-(4-{8-Chloro-3-[(1S)-1-(pyrido[3,2-d]pyrimidin-4-ylamino)ethyl]quinolin-2-yl}piperazin-1-yl)ethanone To a solution of Intermediate 21 (130 mg, 0.3 mmol) in 1,4-dioxane (1 mL) was added HCl (5.0 mL; 4M in 1,4-dioxane). The reaction mixture was stirred at r.t. for 1 h, then the excess solvent was removed in vacuo. The resulting material was dissolved in n-BuOH (2.5 mL), and DIPEA (0.78 mg, 0.6 mmol) and 4-chloropyrido[3,2-d]pyrimidine (50 mg, 0.33 mmol) were added. The reaction mixture was heated at 120° C. for 16 h and the solvent was removed in vacuo. The residue was purified by preparative HPLC to afford the title compound (26 mg, 19%) as an off-white solid. $\delta_H$ (CDCl$_3$) 8.76 (1H, dd, J 4.27, 1.56 Hz), 8.59 (1H, s), 8.18-8.12 (2H, m), 7.73-7.68 (2H, m), 7.65-7.57 (2H, m), 7.30 (1H, t, J 7.82 Hz), 5.87-5.77 (1H, m), 3.98-3.62 (6H, m), 3.40-3.32 (1H, m), 3.31-3.24 (1H, m), 2.18 (3H, s), 1.71 (3H, d, J 6.73 Hz). LCMS (ES+) 462/464 (M+H)$^+$, RT 3.19 minutes (Method 1).

Example 16

4-{7-Fluoro-8-methyl-3-[(1S)-1-(pyrido[3,2-d]pyrimidin-4-ylamino)ethyl]quinolin-2-yl}piperazine-1-carboxamide Intermediate 22 (50 mg, 0.151 mmol), 4-chloropyrido[3,2-d]pyrimidine (37.5 mg, 0.226 mmol), DIPEA (0.079 mL, 0.453 mmol) and n-BuOH (1 mL) were combined and heated under microwave irradiation at 140° C. for 1 h. After cooling, the mixture was dissolved in EtOAc (100 mL) and washed with saturated brine (3×20 mL). The organic layer was separated, dried (MgSO$_4$), filtered and concentrated in vacuo. Purification by preparative HPLC gave the title compound (3.7 mg, 5%) as a white solid. $\delta_H$ (DMSO-$d_6$) 8.82-8.77 (2H, m), 8.44 (1H, s), 8.41 (1H, s), 8.07 (1H, dd, J 8.46, 1.52 Hz), 7.80 (1H, dd, J 8.46, 4.25 Hz), 7.63 (1H, dd, J 8.92, 6.31 Hz), 7.22 (1H, t, J 9.13 Hz), 5.96 (2H, s), 5.82-5.75 (1H, m), 3.57-3.45 (4H, m), 3.44-3.37 (2H, m), 3.04-2.96 (2H, m), 2.47 (3H, d, J 2.24 Hz), 1.55 (3H, d, J 6.71 Hz). LCMS (ES+) 461 (M+H)$^+$, RT 2.50 minutes (Method 2).

Example 17

(Cyclopropyl)(4-{7-fluoro-8-methyl-3-[(1S)-1-(pyrido[3,2-d]pyrimidin-4-ylamino)ethyl]-quinolin-2-yl}piperazin-1-yl)methanone To a solution of Intermediate 9 (500 mg, 1.48 mmol) in NMP (6 mL) were added (cyclopropyl)(piperazin-1-yl)methanone (455 mg, 2.95 mmol) and DIPEA (1.3 mL), and the mixture was heated at 140° C. for 16 h. The reaction mixture was taken up in EtOAc (150 mL) and water (50 mL)

and the organic layer was washed with water (2×50 mL) and brine (50 mL). The organic layer was separated and dried (phase separation cartridge), and the solvent was removed in vacuo. Purification by column chromatography (SiO$_2$, 10-20% EtOAc in isohexane) gave a beige solid (390 mg, 57%). To a solution of this material (390 mg, 0.85 mmol) in DCM (6 mL) was added TFA (3 mL) and the resulting solution was stirred at r.t. for 15 minutes. The solvents were removed in vacuo. The residue was dissolved in MeOH (5 mL), then placed on an SCX cartridge, washed (MeOH), eluted (7M ammonia in MeOH) and concentrated in vacuo to afford a white solid (304 mg, 100%). To a portion of this material (60 mg, 0.17 mmol) in NMP (1.2 mL) were added DIPEA (0.14 mL) and 4-chloropyrido[3,2-d]pyrimidine (33 mg, 0.2 mmol). The resulting solution was heated under microwave irradiation at 150° C. for 1 h. Purification by preparative HPLC afforded the title compound (51 mg, 61%) as a beige solid. $\delta_H$ (DMSO-d$_6$) 8.93-8.88 (2H, m), 8.54 (2H, d, J 11.51 Hz), 8.17 (1H, dd, J 8.46, 1.58 Hz), 7.90 (1H, dd, J 8.46, 4.25 Hz), 7.74 (1H, dd, J 8.94, 6.26 Hz), 7.33 (1H, t, J 9.12 Hz), 5.91 (1H, m), 4.05-3.13 (8H, s), 2.58 (3H, m), 2.12-2.07 (1H, m), 1.67 (3H, d, J 6.71 Hz), 0.90-0.73 (4H, m). LCMS (ES+) 486 (M+H)$^+$, RT 2.78 minutes (Method 2).

Example 18

(4-{7-Fluoro-8-methyl-3-[(1S)-1-(pyrido[3,2-d]pyrimidin-4-ylamino)ethyl]quinolin-2-yl}piperazin-1-yl) acetic acid Intermediate 9 (700 mg, 2.06 mmol), ethyl 1-piperazineacetate (0.5 g), n-BuOH (10 mL) and DIPEA (2 mL) were combined in a sealed tube and heated at 130° C. for 12 days. The reaction mixture was cooled, concentrated onto silica and purified by column chromatography (SiO$_2$, 0-100% EtOAc in isohexane). The resulting material, EtOH (7 mL) and 2M HCl in Et$_2$O (5 mL) were combined and stirred at r.t. for 3 days. The reaction mixture was concentrated to give a pale yellow solid. A portion of this material (50 mg), n-BuOH (6 mL), DIPEA (1 mL) and 4-chloropyrido[3,2-d]pyrimidine (50 mg, 0.25 mmol) were combined in a sealed tube and heated under microwave irradiation at 160° C. for 2 h. 15% NaOH solution (0.2 mL) was added to the reaction mixture, which was stirred at r.t. for 3 days. The mixture was concentrated to dryness and purified by preparative HPLC to give the title compound (38.1 mg) as a brown glass. $\delta_H$ (DMSO-d$_6$) 8.93-8.85 (2H, m), 8.53 (1H, s), 8.49 (1H, s), 8.17 (1H, dd, J 8.46, 1.58 Hz), 7.90 (1H, dd, J 8.46, 4.25 Hz), 7.72 (1H, dd, J 8.91, 6.29 Hz), 7.30 (1H, t, J 9.11 Hz), 5.90-5.81 (1H, m), 3.76-3.65 (2H, m), 3.27 (2H, s), 3.25-3.17 (2H, m), 2.98-2.89 (2H, m), 2.88-2.79 (2H, m), 2.57 (3H, s), 1.64 (3H, d, J 6.69 Hz). LCMS (ES+) 476 (M+H)$^+$, RT 2.43 minutes (Method 1).

Example 19

1-(4-{8-Chloro-3-[(1S)-1-(pyrido[3,2-d]pyrimidin-4-ylamino)ethyl]quinolin-2-yl}piperazin-1-yl)-2-hydroxyethanone Intermediate 4 (700 mg, 2.05 mmol), 2-hydroxy-1-(piperazin-1-yl)ethanone hydrochloride (1.5 g, 8.30 mmol), n-BuOH (10 mL) and DIPEA (4 mL) were combined in a sealed tube and heated at 130° C. for 7 days. The reaction mixture was cooled, concentrated onto silica and purified by column chromatography (SiO$_2$, 0-10% MeOH in EtOAc) to give a yellow gum (318 mg). This material, MeOH (5 mL) and 2M HCl in Et$_2$O (5 mL) were combined and stirred at r.t. for 24 h. The reaction mixture was concentrated in vacuo to give a yellow glass. A portion of this material (50 mg, 0.13 mmol), n-BuOH (6 mL), DIPEA (1 mL) and 4-chloropyrido[3,2-d]pyrimidine (50 mg, 0.25 mmol) were combined in a sealed tube and heated under microwave irradiation at 160° C. for 2 h. The reaction mixture was concentrated to dryness and purified by preparative HPLC to give the title compound (9 mg, 15%) as a tan glass. $\delta_H$ (DMSO-d$_6$) 8.95 (1H, d, J 7.89 Hz), 8.89 (1H, dd, J 4.25, 1.58 Hz), 8.58-8.49 (2H, m), 8.15 (1H, dd, J 8.46, 1.58 Hz), 7.88 (1H, dd, J 8.47, 4.25 Hz), 7.82-7.77 (2H, m), 7.39 (1H, t, J 7.82 Hz), 5.90-5.81 (1H, m), 4.61 (1H, t, J 5.46 Hz), 4.20-4.15 (2H, m), 3.86-3.13 (8H, m), 1.64 (3H, d, J 6.73 Hz). LCMS (ES+) 478/480 (M+H)$^+$, RT 3.04 minutes (Method 1).

Example 20

1-(4-{8-Chloro-3-[(1S)-1-(pyrido[3,2-c]pyrimidin-4-ylamino)ethyl]quinolin-2-yl}piperazin-1-yl)-2-(dimethylamino)ethanone Intermediate 4 (700 mg, 2.05 mmol), 2-(dimethylamino)-1-(piperazin-1-yl)ethanone (500 mg), n-BuOH (10 mL) and DIPEA (4 mL) were combined in a sealed tube and heated at 130° C. for 10 days. The reaction mixture was cooled, concentrated onto silica and purified by column chromatography (SiO$_2$, 0-10% MeOH in EtOAc) to give a cream solid (610 mg). This material, MeOH (6 mL) and 2M HCl in Et$_2$O (6 mL) were combined and stirred at r.t. for 24 h. The reaction mixture was concentrated in vacuo to give a yellow foam. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated under microwave irradiation at 160° C. for 2 h. The reaction mixture was concentrated to dryness and purified by preparative HPLC to give the title compound (22.2 mg, 37%) as a tan glass. $\delta_H$ (DMSO-d$_6$) 8.97 (1H, d, J 7.89 Hz), 8.89 (1H, dd, J 4.25, 1.59 Hz), 8.54 (1H, s), 8.52 (1H, s), 8.15 (1H, dd, J 8.46, 1.59 Hz), 7.88 (1H, dd, J 8.47, 4.25 Hz), 7.82-7.76 (2H, m), 7.39 (1H, t, J 7.82 Hz), 5.91-5.81 (1H, m), 3.94-3.07 (10H, m), 2.21 (6H, s), 1.64 (3H, d, J 6.72 Hz). LCMS (ES+) 505/507 (M+H)$^+$, RT 1.96 minutes (Method 2).

Example 21

1-{7-Fluoro-8-methyl-3-[(1S)-1-(pyrido[3,2-d]pyrimidin-4-ylamino)ethyl]quinolin-2-yl}piperidine-4-carboxamide formic acid salt Intermediate 9 (700 mg, 2.06 mmol), 4-piperidinecarboxamide (0.5 g), n-BuOH (10 mL) and DIPEA (4 mL) were combined in a sealed tube and heated at 130° C. for 12 days. The reaction mixture was cooled, concentrated onto silica and purified by column chromatography (SiO$_2$, 0-10% MeOH in EtOAc) to give a clear gum (823 mg). This material, MeOH (10 mL) and 2M HCl in Et$_2$O (7 mL) were combined and stirred at r.t. for 24 h. The mixture was concentrated in vacuo to give a yellow solid. A portion of this material (60 mg), n-BuOH (6 mL), DIPEA (1 mL) and 4-chloropyrido[3,2-d]pyrimidine (50 mg, 0.25 mmol) were combined in a sealed tube and heated under microwave irradiation at 160° C. for 2 h. The reaction mixture was then concentrated to dryness and purified by preparative HPLC to give the title compound (17.5 mg) as a brown solid. $\delta_H$ (DMSO-d$_6$) 8.90 (1H, dd, J 4.26, 1.56 Hz), 8.85 (1H, d, J 7.99 Hz), 8.52 (1H, s), 8.46 (1H, s), 8.40 (1H, s, HCOOH), 8.17 (1H, dd, J 8.46, 1.56 Hz), 7.90 (1H, dd, J 8.46, 4.25 Hz), 7.70 (1H, dd, J 8.92, 6.33 Hz), 7.36-7.24 (2H, m), 6.82 (1H, s), 5.89-5.80 (1H, m), 4.16-4.08 (1H, m), 3.70-3.61 (1H, m), 3.21-3.13 (1H, m), 2.78-2.29 (1H, m), 2.56 (3H, s), 2.42-2.32 (1H, m), 1.99-1.78 (4H, m), 1.65 (3H, d, J 6.71 Hz). LCMS (ES+) 460 (M+H)$^+$, RT 3.19 minutes (Method 1).

Example 22

1-{7-Fluoro-8-methyl-3-[(1S)-1-(pyrido[3,2-d]pyrimidin-4-ylamino)ethyl]quinolin-2-yl}piperidine-4-carboxylic acid Intermediate 9 (700 mg, 2.06 mmol), methyl 4-piperidinecarboxylate hydrochloride (500 mg, 2.78 mmol), n-BuOH (10 mL) and DIPEA (4 mL) were combined in a sealed tube and heated at 130° C. for 12 days. The reaction mixture was cooled, concentrated onto silica and purified by column chromatography (SiO$_2$, 0-10% MeOH in EtOAc). The resulting material, MeOH (10 mL) and 2M HCl in Et$_2$O (6 mL) were combined and stirred at r.t. for 24 h. The reaction mixture was concentrated to give a tan foam. A portion of this material (50 mg), n-BuOH (6 mL), DIPEA (1 mL) and 4-chloropyrido[3,2-d]pyrimidine (50 mg, 0.25 mmol) were combined in a sealed tube and heated under microwave irradiation at 160° C. for 2 h. 15% NaOH solution (0.2 ml) was added to the reaction mixture, which was stirred at r.t. for 3 days. The reaction mixture was concentrated to dryness and purified by preparative HPLC to give the title compound (15.3 mg) as a white solid. $\delta_H$ (DMSO-d$_6$) 8.93-8.83 (2H, m), 8.52 (1H, s), 8.46 (1H, s), 8.16 (1H, dd, J 8.46, 1.55 Hz), 7.89 (1H, dd, J 8.47, 4.25 Hz), 7.70 (1H, dd, J 8.90, 6.35 Hz), 7.29 (1H, t, J 9.12 Hz), 5.88-5.79 (1H, m), 4.08-3.99 (1H, m), 3.63-3.54 (1H, m), 3.28-3.19 (1H, m), 2.86-2.77 (1H, m), 2.57 (3H, s), 2.54-2.45 (1H, m), 2.11-2.03 (1H, m), 1.97-1.80 (3H, m), 1.65 (3H, d, J 6.71 Hz). LCMS (ES+) 461 (M+H)$^+$, RT 2.31 minutes (Method 1).

Example 23

1-{7-Fluoro-8-methyl-3-[(1S)-1-(pyrido[3,2-d]pyrimidin-4-ylamino)ethyl]quinolin-2-yl}-N-methylpiperidine-4-carboxamide Intermediate 9 (700 mg, 2.06 mmol), piperidine-4-carboxylic acid methylamide (426 mg, 3 mmol), n-BuOH (10 mL) and DIPEA (3 mL) were combined in a sealed tube and heated at 130° C. for 20 days. The reaction mixture was cooled, concentrated onto silica and purified by column chromatography (SiO$_2$, 0-10% MeOH in EtOAc) to give a white solid. This material, MeOH (10 mL) and 2M HCl in Et$_2$O (5 mL) were combined and stirred at r.t. for 4 days. The reaction mixture was concentrated to give a yellow solid. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated at 130° C. for 16 h. The reaction mixture was then concentrated to dryness and purified by preparative HPLC to give the title compound (40.1 mg, 71%) as a brown solid. $\delta_H$ (DMSO-d$_6$) 8.93-8.83 (2H, m), 8.52 (1H, s), 8.46 (1H, s), 8.17 (1H, dd, J 8.47, 1.54 Hz), 7.90 (1H, dd, J 8.47, 4.25 Hz), 7.80 (1H, m), 7.70 (1H, dd, J 8.91, 6.34 Hz), 7.29 (1H, t, J 9.12 Hz), 5.86-5.79 (1H, m), 4.17-4.07 (1H, m), 3.70-3.62 (1H, m), 3.18-3.10 (1H, m), 2.73 (1H, t, J 11.87 Hz), 2.64 (3H, d, J 4.51 Hz), 2.56 (3H, s), 2.42-2.32 (1H, m), 2.04-1.76 (4H, m), 1.65 (3H, d, J 6.72 Hz). LCMS (ES+) 474 (M+H)$^+$, RT 3.86 minutes (Method 1).

Example 24

2-(Dimethylamino)-1-(4-{7-fluoro-8-methyl-3-[(1S)-1-(pyrido[3,2-d]pyrimidin-4-ylamino)ethyl]quinolin-2-yl}piperazin-1-yl)ethanone formic acid salt Intermediate 9 (700 mg, 2.06 mmol), 2-(dimethylamino)-1-(piperazin-1-yl)ethanone (500 mg), n-BuOH (10 mL) and DIPEA (2 mL) were combined in a sealed tube and heated at 130° C. for 13 days. The reaction mixture was cooled, concentrated onto silica and purified by column chromatography (SiO$_2$, 0-10% MeOH in EtOAc) to give a white solid. This material, MeOH (8 mL) and 2M HCl in Et$_2$O (4 mL) were combined and stirred at r.t. for 2 days. The reaction mixture was concentrated in vacuo to give a yellow foam. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated at 130° C. for 16 h. The reaction mixture was then concentrated to dryness and purified by preparative HPLC to give the title compound (28 mg, 43%) as a white solid. $\delta_H$ (DMSO-d$_6$) 8.92-8.89 (2H, m), 8.55 (1H, s), 8.52 (1H, s), 8.37 (1H, s, HCOOH), 8.17 (1H, dd, J 8.46, 1.56 Hz), 7.90 (1H, dd, J 8.46, 4.25 Hz), 7.73 (1H, dd, J 8.91, 6.29 Hz), 7.32 (1H, t, J 9.12 Hz), 5.94-5.85 (1H, m), 3.95-3.86 (1H, m), 3.80-3.68 (3H, m), 3.58-3.57 (2H, m), 3.26-3.12 (4H, m), 2.57 (3H, s), 2.24 (6H, s), 1.66 (3H, d, J 6.72 Hz). LCMS (ES+) 503 (M+H)$^+$, RT 2.04 minutes (Method 2).

Example 25

1-(4-{8-Chloro-3-[(1S)-1-(pyrido[3,4-d]pyrimidin-4-ylamino)ethyl]quinolin-2-yl}piperazin-1-yl)-2-(dimethylamino)ethanone Intermediate 4 (700 mg, 2.05 mmol), 2-(dimethylamino)-1-(piperazin-1-yl)ethanone (500 mg), n-BuOH (10 mL) and DIPEA (4 mL) were combined in a sealed tube and heated at 130° C. for 10 days. The reaction mixture was cooled, concentrated onto silica and purified by column chromatography (SiO$_2$, 0-10% MeOH in EtOAc) to give a cream solid (610 mg). This material, MeOH (6 mL) and 2M HCl in Et$_2$O (6 mL) were combined and stirred at r.t. for 24 h. The reaction mixture was concentrated in vacuo to give a yellow foam. A portion of this material (50 mg, 0.12 mmol), n-BuOH (6 mL), DIPEA (1 mL) and 4-chloropyrido[3,4-d]pyrimidine (50 mg, 0.25 mmol) were combined in a sealed tube and heated at 130° C. for 3 days. The reaction mixture was concentrated to dryness and purified by preparative HPLC to give the title compound (26 mg, 43%) as a brown glass. $\delta_H$ (DMSO-d$_6$) 9.14 (1H, s), 8.96 (1H, d, J 6.86 Hz), 8.71 (1H, d, J 5.61 Hz), 8.64 (1H, s), 8.47-8.40 (2H, m), 7.87-7.80 (2H, m), 7.42 (1H, t, J 7.82 Hz), 5.89-5.80 (1H, m), 3.94-3.10 (10H, m), 2.24 (6H, s), 1.66 (3H, d, J 6.70 Hz). LCMS (ES+) 505/507 (M+H)$^+$, RT 2.61 minutes (Method 1).

Example 26

1-{7-Fluoro-8-methyl-3-[(1S)-1-(pyrido[3,4-]pyrimidin-4-ylamino)ethyl]quinolin-2-yl}-N-methylpiperidine-4-carboxamide Intermediate 9 (700 mg, 2.06 mmol), piperidine-4-carboxylic acid methylamide (426 mg, 3 mmol), n-BuOH (10 mL) and DIPEA (3 mL) were combined in a sealed tube and heated at 130° C. for 20 days. The reaction mixture was cooled, concentrated onto silica and purified by column chromatography (SiO$_2$, 0-10% MeOH in EtOAc) to give a white solid. This material, MeOH (10 mL) and 2M HCl in Et$_2$O (5 mL) were combined and stirred at r.t. for 4 days. The reaction mixture was concentrated to give a yellow solid. A portion of this material (50 mg, 0.12 mmol), n-BuOH (6 mL), DIPEA (1 mL) and 4-chloropyrido[3,4-d]pyrimidine (50 mg, 0.25 mmol) were combined in a sealed tube and heated at 130° C. for 16 h. The reaction mixture was then concentrated to dryness and purified by preparative HPLC to give the title compound (31.6 mg, 56%) as a brown glass. $\delta_H$ (DMSO-d$_6$) 9.13 (1H, s), 8.90 (1H, d, J 6.93 Hz), 8.70 (1H, d, J 5.61 Hz), 8.60 (1H, s), 8.46 (1H, d, J 5.69 Hz), 8.30 (1H, s), 7.80-7.71 (2H, m), 7.29 (1H, t, J 9.12 Hz), 5.85-5.76 (1H, m), 4.21-4.14 (1H, m), 3.71-3.63 (1H, m), 3.17 (1H, t, J 12.47 Hz), 2.71 (1H, t, J 11.21 Hz), 2.63 (3H, d, J 4.51 Hz), 2.57 (3H, s), 2.41-2.31 (1H, m), 2.00-1.75 (4H, m), 1.63 (3H, d, J 6.70 Hz). LCMS (ES+) 474 (M+H)$^+$, RT 3.54 minutes (Method 1).

Example 27

2-(Dimethylamino)-1-(4-{7-fluoro-8-methyl-3-[(1S)-1-(pyrido[3,4-d]pyrimidin-4-ylamino)ethyl]quinolin-2-yl}piperazin-1-yl)ethanone Intermediate 9 (700 mg, 2.06 mmol), 2-(dimethylamino)-1-(piperazin-1-yl)ethanone (500 mg), n-BuOH (10 mL) and DIPEA (2 mL) were combined in a sealed tube and heated at 130° C. for 13 days. The reaction mixture was cooled, concentrated onto silica and purified by column chromatography (SiO$_2$, 0-10% MeOH in EtOAc) to give a white solid. This material, MeOH (8 mL) and 2M HCl in Et$_2$O (4 mL) were combined and stirred at r.t. for 2 days. The reaction mixture was concentrated in vacuo to give a yellow foam. A portion of this material (50 mg, 0.12 mmol), n-BuOH (6 mL), DIPEA (1 mL) and 4-chloropyrido[3,4-d]pyrimidine (50 mg, 0.25 mmol) were combined in a sealed tube and heated at 130° C. for 16 h. The reaction mixture was concentrated to dryness and purified by preparative HPLC to give the title compound (20.3 mg, 34%) as a brown glass. $\delta_H$ (DMSO-d$_6$) 9.13 (1H, s), 8.93 (1H, d, J 6.95 Hz), 8.70 (1H, d, J 5.59 Hz), 8.63 (1H, s), 8.45 (1H, d, J 5.67 Hz), 8.36 (1H, s), 7.78 (1H, dd, J 8.93, 6.30 Hz), 7.33 (1H, t, J 9.13 Hz), 5.90-5.81 (1H, m), 3.94-3.06 (10H, m), 2.57 (3H, s), 2.24 (6H, s), 1.65 (3H, d, J 6.68 Hz). LCMS (ES+) 503 (M+H)$^+$, RT 3.11 minutes (Method 1).

Example 28

1-{7-Fluoro-8-methyl-3-[(1S)-1-(pyrido[3,4-d]pyrimidin-4-ylamino)ethyl]quinolin-2-yl}piperidine-4-carboxamide Intermediate 9 (700 mg, 2.06 mmol), 4-piperidinecarboxamide (0.5 g), n-BuOH (10 mL) and DIPEA (4 mL) were combined in a sealed tube and heated at 130° C. for 12 days. The reaction mixture was cooled, concentrated onto silica and purified by column chromatography (SiO$_2$, 0-10% MeOH in EtOAc) to give a clear gum (823 mg). This material, MeOH (10 mL) and 2M HCl in Et$_2$O (7 mL) were combined and stirred at r.t. for 24 h. The mixture was concentrated in vacuo to give a yellow solid. A portion of this material (50 mg), n-BuOH (6 mL), DIPEA (1 mL) and 4-chloropyrido[3,4-d]pyrimidine (50 mg, 0.25 mmol) were combined in a sealed tube and heated at 130° C. for 16 h. The reaction mixture was concentrated to dryness and purified by preparative HPLC to give the title compound (16.7 mg, 30%) as a tan solid. $\delta_H$ (DMSO-d$_6$) 9.13 (1H, s), 8.91 (1H, d, J 6.96 Hz), 8.70 (1H, d, J 5.61 Hz), 8.60 (1H, s), 8.46 (1H, d, J 5.69 Hz), 8.30 (1H, s), 7.74 (1H, dd, J 8.91, 6.34 Hz), 7.34-7.23 (2H, m), 6.82 (1H, s), 5.84-5.76 (1H, m), 4.21-4.13 (1H, m), 3.71-3.62 (1H, m), 3.23-3.11 (1H, m), 2.72 (1H, t, J 11.88 Hz), 2.57 (3H, m), 2.41-2.31 (1H, m), 1.97-1.73 (4H, m), 1.63 (3H, d, J 6.69 Hz). LCMS (ES+) 460 (M+H)$^+$, RT 3.42 minutes (Method 1).

Example 29

(4-{7-Fluoro-8-methyl-3-[(1S)-1-(pyrido[3,4-d]pyrimidin-4-ylamino)ethyl]quinolin-2-yl}piperazin-1-yl)acetic acid Intermediate 9 (700 mg, 2.06 mmol), ethyl 1-piperazineacetate (0.5 g), n-BuOH (10 mL) and DIPEA (2 mL) were combined in a sealed tube and heated at 130° C. for 12 days. The reaction mixture was cooled, concentrated onto silica and purified by column chromatography (SiO$_2$, 0-100% EtOAc in isohexane). The resulting material, EtOH (7 mL) and 2M HCl in Et$_2$O (5 mL) were combined and stirred at r.t. for 3 days. The reaction mixture was concentrated to give a pale yellow solid. A portion of this material (50 mg), n-BuOH (6 mL), DIPEA (1 mL) and 4-chloropyrido[3,4-d]pyrimidine (50 mg, 0.25 mmol) were combined in a sealed tube and heated at 130° C. for 3 days. 15% NaOH solution (0.2 mL) was added to the reaction mixture which was stirred at r.t. for 2 days. The reaction mixture was then concentrated to dryness and purified by preparative HPLC to give the title compound (26.7 mg) as a light brown solid. $\delta_H$ (DMSO-d$_6$) 9.12 (1H, s), 8.91 (1H, d, J 6.97 Hz), 8.70 (1H, d, J 5.61 Hz), 8.61 (1H, s), 8.44 (1H, d, J 5.70 Hz), 8.33 (1H, s), 7.76 (1H, dd, J 8.90, 6.33 Hz), 7.30 (1H, t, J 9.12 Hz), 5.87-5.78 (1H, m), 3.76-3.67 (2H, m), 3.27-3.16 (4H, m), 2.93-2.85 (2H, m), 2.84-2.74 (2H, m), 2.57 (3H, s), 1.62 (3H, d, J 6.67 Hz). LCMS (ES+) 476 (M+H)$^+$, RT 2.45 minutes (Method 1).

Example 30

1-{8-Chloro-3-[(1S)-1-(pyrido[3,2-d]pyrimidin-4-ylamino)ethyl]quinolin-2-yl}-N-methylpiperidine-4-carboxamide Intermediate 4 (700 mg, 2.06 mmol), piperidine-4-carboxylic acid methylamide (426 mg, 3 mmol), n-BuOH (10 mL) and DIPEA (3 mL) were combined in a sealed tube and heated at 130° C. for 10 days. The reaction mixture was cooled, concentrated onto silica and purified by column chromatography (SiO$_2$, 0-10% MeOH in EtOAc) to give a white solid. This material, MeOH (10 mL) and 2M HCl in Et$_2$O (5 mL) were combined and stirred at r.t. for 3 days. The reaction mixture was concentrated to give a yellow solid. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated at 130° C. for 16 h. The reaction mixture was then concentrated to dryness and purified by preparative HPLC to give the title compound (49.5 mg, 87%) as a brown glass. $\delta_H$ (DMSO-d$_6$) 8.91 (2H, m), 8.52 (2H, m), 8.17 (1H, d, J 8.47 Hz), 7.90 (1H, dd, J 8.47, 4.24 Hz), 7.79 (3H, m), 7.38 (1H, t, J 7.80 Hz), 5.88-5.80 (1H, m), 4.21-4.15 (1H, m), 3.74-3.66 (1H, m), 3.21-3.14 (1H, m), 2.81-2.72 (1H, m), 2.64 (3H, d, J 4.48 Hz), 2.42-2.33 (1H, m), 2.05-1.78 (4H, m), 1.66 (3H, d, J 6.69 Hz). LCMS (ES+) 476/478 (M+H)$^+$, RT 2.49 minutes (Method 2).

Example 31

1-{7-Fluoro-8-methyl-3-[(1S)-1-(pyrido[3,2-d]pyrimidin-4-ylamino)ethyl]quinolin-2-yl}piperidin-4-ol Intermediate 9 (700 mg, 2.06 mmol), 4-hydroxypiperidine (300 mg, 3 mmol), n-BuOH (10 mL) and DIPEA (3 mL) were combined in a sealed tube and heated at 130° C. for 14 days. The reaction mixture was cooled, concentrated onto silica and purified by column chromatography (SiO$_2$, 0-10% MeOH in EtOAc) to give a clear gum. This material, MeOH (6 mL) and 2M HCl in Et$_2$O (6 mL) were combined and stirred at r.t. for 1 day. The reaction mixture was concentrated in vacuo to give a yellow foam. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated at 130° C. for 16 h. The reaction mixture was then concentrated to dryness and purified by preparative HPLC to give the title compound (49.1 mg, 95%) as a tan solid. $\delta_H$(DMSO-d$_6$) 8.90 (1H, dd, J 4.25, 1.58 Hz), 8.80 (1H, d, J 7.98 Hz), 8.53 (1H, s), 8.45 (1H, s), 8.17 (1H, dd, J 8.46, 1.58 Hz), 7.90 (1H, dd, J 8.47, 4.25 Hz), 7.70 (1H, dd, J 8.91, 6.34 Hz), 7.28 (1H, t, J 9.13 Hz), 5.89-5.81 (1H, m), 4.72 (1H, d, J 4.14 Hz), 3.92 (1H, d, J 12.64 Hz), 3.74 (1H, s), 3.51 (1H, d, J 12.66 Hz), 3.33-3.25 (1H, m), 2.88 (1H, t, J 11.14 Hz), 2.56 (3H, s), 2.06-1.98 (1H, m), 1.95-1.87 (1H, m), 1.80-1.59 (5H, m). LCMS (ES+) 433 (M+H)$^+$, RT 3.96 minutes (Method 1).

Example 32

1-{8-Chloro-3-[(1S)-1-(pyrido[3,2-d]pyrimidin-4-ylamino)ethyl]quinolin-2-yl}piperidin-4-ol Intermediate 4 (700 mg, 2.06 mmol), 4-hydroxypiperidine (300 mg, 3 mmol), n-BuOH (10 mL) and DIPEA (3 mL) were combined in a sealed tube and heated at 130° C. for 7 days. The reaction mixture was cooled, concentrated onto silica and purified by column chromatography (SiO$_2$, 0-10% MeOH in EtOAc) to give a clear oil. This material, MeOH (10 mL) and 2M HCl in Et$_2$O (4 mL) were combined and stirred at r.t. for 2 days. The reaction mixture was concentrated in vacuo to give a yellow foam. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated at 130° C. for 16 h. The reaction mixture was then concentrated to dryness and purified by preparative HPLC to give the title compound (43.4 mg, 83%) as an off-white solid. $\delta_H$(DMSO-d$_6$) 8.93-8.87 (2H, m), 8.53 (1H, s), 8.50 (1H, s), 8.17 (1H, dd, J 8.46, 1.57 Hz), 7.90 (1H, dd, J 8.47, 4.25 Hz), 7.82-7.76 (2H, m), 7.37 (1H, t, J 7.81 Hz), 5.89-5.80 (1H, m), 4.74 (1H, d, J 4.24 Hz), 3.98 (1H, d, J 12.71 Hz), 3.79-3.71 (1H, m), 3.55 (1H, d, J 12.75 Hz), 3.36-3.28 (1H, m), 2.92 (1H, t, J 11.17 Hz), 2.06-1.98 (1H, m), 1.96-1.88 (1H, m), 1.82-1.71 (1H, m), 1-71-1.60 (4H, m). LCMS (ES+) 435/437 (M+H)$^+$, RT 3.24 minutes (Method 1).

Example 33

2-(4-{8-Chloro-3-[(1S)-1-(pyrido[3,2-d]pyrimidin-4-ylamino)ethyl]quinolin-2-yl}piperazin-1-yl)acetamide Intermediate 4 (700 mg, 2.06 mmol), 2-(piperazin-1-yl)acetamide hydrochloride (500 mg), n-BuOH (10 mL) and DIPEA (4 mL) were combined in a sealed tube and heated at 130° C. for 16 days. The reaction mixture was cooled, concentrated onto silica and purified by column chromatography (SiO$_2$, 0-10% MeOH in EtOAc) to give a clear gum. This material, MeOH (6 mL) and 2M HCl in Et$_2$O (4 mL) were combined and stirred at r.t. for 1 day. The reaction mixture was concentrated to give a yellow foam. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated at 130° C. for 16 h. The reaction mixture was concentrated to dryness and purified by preparative HPLC to give the title compound (37.2 mg, 65%) as a tan glass. $\delta_H$(DMSO-d$_6$) 8.95-8.88 (2H, m), 8.53 (2H, s), 8.17 (1H, dd, J 8.46, 1.57 Hz), 7.90 (1H, dd, J 8.47, 4.25 Hz), 7.84-7.78 (2H, m), 7.40 (1H, t, J 7.81 Hz), 7.31 (1H, s), 7.18 (1H, s), 5.90-5.81 (1H, m), 3.80-3.71 (2H, m), 3.29-3.21 (2H, m), 3.04-2.95 (2H, m), 2.83-2.75 (2H, m), 2.73-2.65 (2H, m), 1.65 (3H, d, J 6.72 Hz). LCMS (ES+) 477/479 (M+H)$^+$, RT 3.09 minutes (Method 1).

Example 34

2-(4-{7-Fluoro-8-methyl-3-[(1S)-1-(pyrido[3,2-d]pyrimidin-4-ylamino)ethyl]quinolin-2-yl}piperazin-1-yl)-N-methylacetamide Intermediate 9 (700 mg, 2.06 mmol), N-methyl-2-(piperazin-1-yl)acetamide bis(hydrochloride) (500 mg), n-BuOH (10 mL) and DIPEA (4 mL) were combined in a sealed tube and heated at 130° C. for 30 days. The reaction mixture was cooled, concentrated onto silica and purified by column chromatography (SiO$_2$, 0-10% MeOH in EtOAc) to give a clear gum. This material, MeOH (5 mL) and 2M HCl in Et$_2$O (5 mL) were combined and stirred at r.t. for 3 days. The reaction mixture was concentrated in vacuo to give a beige solid. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated to 120° C. for 16 h. The reaction mixture was then concentrated to dryness and purified by preparative HPLC to give the title compound (38 mg, 65%) as a tan glass. $\delta_H$(DMSO-d$_6$) 8.92-8.83 (2H, m), 8.53 (1H, s), 8.48 (1H, s), 8.17 (1H, dd, J 8.46, 1.56 Hz), 7.90 (1H, dd, J 8.47, 4.25 Hz), 7.80-7.68 (2H, m), 7.31 (1H, t, J 9.12 Hz), 5.90-5.81 (1H, m), 3.76-3.68 (2H, m), 3.26-3.17 (2H, m), 3.08-2.99 (2H, m), 2.81-2.73 (2H, m), 2.71-2.63 (5H, m), 2.58 (3H, s), 1.64 (3H, d, J 6.71 Hz). LCMS (ES+) 489 (M+H)$^+$, RT 2.48 minutes (Method 2).

Example 35

2-(4-{8-Chloro-3-[(1S)-1-(pyrido[3,2-d]pyrimidin-4-ylamino)ethyl]quinolin-2-yl}piperazin-1-yl)-N-methylacetamide Intermediate 4 (700 mg, 2.06 mmol), N-methyl-2-(piperazin-1-yl)acetamide bis(hydrochloride) (500 mg), n-BuOH (10 mL) and DIPEA (4 mL) were combined in a sealed tube and heated at 130° C. for 30 days. The reaction mixture was cooled, concentrated onto silica and purified by column chromatography (SiO$_2$, 0-10% MeOH in EtOAc) to give an off-white foam. This material, MeOH (5 mL) and 2M HCl in Et$_2$O (5 mL) were combined and stirred at r.t. for 3 days. The reaction mixture was concentrated in vacuo to give a beige solid. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated at 130° C. for 16 h. The reaction mixture was concentrated to dryness and purified by preparative HPLC to give the title compound (44.5 mg, 76%) as a tan glass. $\delta_H$(DMSO-d$_6$) 8.95-8.88 (2H, m), 8.53 (2H, d, J 1.51 Hz), 8.17 (1H, dd, J 8.47, 1.57 Hz), 7.90 (1H, dd, J 8.47, 4.25 Hz), 7.83-7.78 (3H, m), 7.40 (1H, t, J 7.81 Hz), 5.90-5.81 (1H, m), 3.81-3.72 (2H, m), 3.29-3.21 (2H, m), 3.09-2.98 (2H, m), 2.81-2.73 (2H, m), 2.71-2.63 (5H, m), 1.65 (3H, d, J 6.72 Hz). LCMS (ES+) 491/493 (M+H)$^+$, RT 1.86 minutes (Method 2).

Example 36

2-(4-{7-Fluoro-8-methyl-3-[(1S)-1-(pyrido[3,2-d]pyrimidin-4-ylamino)ethyl]quinolin-2-yl}piperazin-1-yl)acetamide Intermediate 9 (700 mg, 2.06 mmol), 2-(piperazin-1-yl)acetamide hydrochloride (500 mg), n-BuOH (10 mL) and DIPEA (4 mL) were combined in a sealed tube and heated at 130° C. for 30 days. The reaction mixture was cooled, concentrated onto silica and purified by column chromatography ($SiO_2$, 0-10% MeOH in EtOAc) to give a clear gum. This material, MeOH (5 mL) and 2M HCl in $Et_2O$ (5 mL) were combined and stirred at r.t. for 1 day. The reaction mixture was concentrated to give a beige solid. A portion of this material (50 mg, 0.12 mmol), n-BuOH (6 mL), DIPEA (1 mL) and 4-chloropyrido[3,2-d]pyrimidine (50 mg, 0.25 mmol) were combined in a sealed tube and heated at 130° C. for 16 h. The reaction mixture was then concentrated to dryness and purified by preparative HPLC to give the title compound (46.5 mg, 82%) as a brown glass. $\delta_H$ (DMSO-$d_6$) 8.93-8.85 (2H, m), 8.53 (1H, s), 8.48 (1H, s), 8.17 (1H, dd, J 8.46, 1.56 Hz), 7.90 (1H, dd, J 8.46, 4.25 Hz), 7.72 (1H, dd, J 8.91, 6.33 Hz), 7.34-7.26 (2H, m), 7.17 (1H, s), 5.90-5.82 (1H, m), 3.75-3.66 (2H, m), 3.26-3.17 (2H, m), 3.00 (2H, s), 2.82-2.74 (2H, m), 2.73-2.65 (2H, m), 2.58 (3H, s), 1.64 (3H, d, J 6.71 Hz). LCMS (ES+) 475 (M+H)$^+$, RT 1.91 minutes (Method 2).

The invention claimed is:

1. A compound represented by formula (IIA) or an N-oxide thereof, or a pharmaceutically acceptable salt thereof:

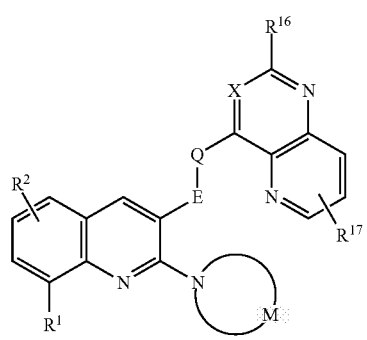

(IIA)

wherein E represents (methyl)methylene;
Q represents N—$R^4$;
M represents the residue of a piperazin-1-yl moiety, optionally substituted by one or more substituents independently selected from heteroaryl, hydroxy, hydroxy($C_{1-6}$)alkyl, oxo, $C_{2-6}$ alkylcarbonyl, hydroxy($C_{1-6}$)alkylcarbonyl, di($C_{1-6}$)alkylamino($C_{1-6}$)alkylcarbonyl, ($C_{3-7}$)cycloalkylcarbonyl, carboxy, carboxy($C_{1-6}$)alkyl, $C_{2-6}$ alkoxycarbonyl, hydroxy($C_{1-6}$)alkylcarbonylamino, ($C_{3-7}$)cycloalkylcarbonylamino, aminocarbonyl, aminocarbonyl($C_{1-6}$)alkyl, $C_{1-6}$ alkylaminocarbonyl and ($C_{1-6}$)alkylaminocarbonyl($C_{1-6}$)alkyl;
$R^1$ and $R^2$ independently represent hydrogen, halogen, cyano, nitro, $C_{1-6}$ alkyl, trifluoromethyl, $C_{3-7}$ cycloalkyl($C_{1-6}$)alkyl, $C_{3-7}$ heterocycloalkyl($C_{1-6}$)alkyl, aryl($C_{1-6}$)-alkyl, heteroaryl($C_{1-6}$)alkyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl;
X represents N or CH; and
$R^{16}$ and $R^{17}$ independently represent hydrogen, $C_{1-6}$ alkyl, amino, $C_{1-6}$ alkylamino or di($C_{1-6}$)alkylamino.

2. A compound represented by formula (IIB) or an N-oxide thereof, or a pharmaceutically acceptable salt thereof:

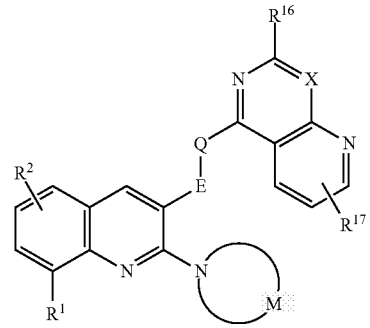

(IIB)

wherein E represents (methyl)methylene;
Q represents N—$R^4$;
M represents the residue of a piperazin-1-yl moiety, optionally substituted by one or more substituents independently selected from heteroaryl, hydroxy, hydroxy($C_{1-6}$)alkyl, oxo, $C_{2-6}$ alkylcarbonyl, hydroxy($C_{1-6}$)alkylcarbonyl, di($C_{1-6}$)alkylamino($C_{1-6}$)alkylcarbonyl, ($C_{3-7}$)cycloalkylcarbonyl, carboxy, carboxy($C_{1-6}$)alkyl, $C_{2-6}$ alkoxycarbonyl, hydroxy($C_{1-6}$)alkylcarbonylamino, ($C_{3-7}$)cycloalkylcarbonylamino, aminocarbonyl, aminocarbonyl($C_{1-6}$)alkyl, $C_{1-6}$ alkylaminocarbonyl and ($C_{1-6}$)alkylaminocarbonl($C_{1-6}$)alkyl,
$R^1$ and $R^2$ independently represent hydrogen, halogen, cyano, nitro, $C_{1-6}$ alkyl, trifluoromethyl, $C_{3-7}$ cycloalkyl($C_{1-6}$)alkyl, $C_{3-7}$ heterocycloalkyl($C_{1-6}$)alkyl, aryl($C_{1-6}$)-alkyl, heteroaryl($C_{1-6}$)alkyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl
X represents N or CH; and
$R^{16}$ and $R^{17}$ independently represent hydrogen, $C_{1-6}$ alkyl, amino, $C_{1-6}$ alkylamino or di($C_{1-6}$)alkylamino.

3. A compound as claimed in claim 1 wherein the moiety of which M is the residue is selected from 4-(pyridin-2-yl)piperazin-1-yl, 4-(pyrazin-2-yl)piperazin-1-yl, 4-(2-hydroxyethyl)piperazin-1-yl, 3-oxopiperazin-1-yl, 4-acetylpiperazin-1-yl, 4-(ethylcarbonyl)piperazin-1-yl, 4-(tert-butylcarbonyl)piperazin-1-yl, 4-(hydroxyacetyl)piperazin-1-yl, 4-(dimethylaminoacetyl)piperazin-1-yl, 4-(cyclopropylcarbonyl)piperazin-1-yl, 4-(carboxymethyl)piperazin-1-yl, 4-(methoxycarbonyl)piperazin-1-yl, 4-(aminocarbonyl)piperazin-1-yl, 4-(aminocarbonylmethyl)piperazin-1-yl and 4-(methylaminocarbonylmethyl)piperazin-1-yl.

4. A compound as claimed in claim 1 wherein $R^1$ represents hydrogen, halogen or $C_{1-6}$ alkyl.

5. A compound as claimed in claim 1 wherein $R^2$ represents hydrogen or halogen.

6. A compound selected from the group consisting of
- (S)-4-{8-chloro-3-[1-(pyrido[3,2-d]pyrimidin-4-ylamino) ethyl]quinolin-2-yl}piperazin-2-one;
- (S)-2-(4-{8-chloro-3-[1-(pyrido[3,2-d]pyrimidin-4-ylamino)ethyl]quinolin-2-yl}piperazin-1-yl)ethanol;
- S)-4-{7-fluoro-8-methyl-3-[1-(pyrido[2,3-d]pyrimidin-4-ylamino)ethyl]quinolin-2-yl}piperazin-2-one;
- (S)-4-{7-fluoro-8-methyl-3-[1-(pyrido[3,2-d]pyrimidin-4-ylamino)ethyl]quinolin-2-yl}piperazin-2-one;
- (S)-1-(4-{7-fluoro-8-methyl-3-[1-(pyrido[3,2-d]pyrimidin-4-ylamino)ethyl]quinolin-2-yl}piperazin-1-yl) ethanone;
- (S)-1-(4-{7-fluoro-8-methyl-3-[1-(1,5-naphthyridin-4-ylamino)ethyl]quinolin-2-yl}piperazin-1-yl)ethanone;
- (S)-N-(1-{7-fluoro-8-methyl-2-[4-(pyridin-2-yl)piperazin-1-yl]quinolin-3-yl}ethyl)pyrido[3,2-d]pyrimidin-4-amine;
- (S)-N-(1-{7-fluoro-8-methyl-2-[4-(pyrazin-2-yl)piperazin-1-yl]quinolin-3-yl}ethyl)pyrido[3,2-d]pyrimidin-4-amine;
- (S)-1-(4-{7-fluoro-8-methyl-3-[1-(pyrido[3,2-d]pyrimidin-4-ylamino)ethyl]quinolin-2-yl}piperazin-1-yl)propan-1-one;
- S)-1-(4-{7-fluoro-8-methyl-3-[1-(pyrido[3,2-d]pyrimidin-4-ylamino)ethyl]quinolin-2-yl}piperazin-1-yl)-2,2-dimethylpropan-1-one;
- (S)-methyl 4-{7-fluoro-8-methyl-3-[1-(pyrido[2,3-d]pyrimidin-4-ylamino)ethyl]quinolin-2-yl}piperazine-1-carboxylate;
- (S)-2-(4-{8-chloro-3-[1-(pyrido[3,2-d]pyrimidin-4-ylamino)ethyl]quinolin-2-yl)}piperazin-1-yl)acetic acid;
- 1-(4-{8-chloro-3-[(1S)-1-(pyrido[3,2-d]pyrimidin-4-ylamino)ethyl]quinolin-2-yl}piperazin-1-yl)ethanone;
- 4-{7-fluoro-8-methyl-3-[(1S)-1-(pyrido[3,2-d]pyrimidin-4-ylamino)ethyl]quinolin-2-yl}piperazine-1-carboxamide;
- (cyclopropyl)(4-{7-fluoro-8-methyl-3-[(1S)-1-(pyrido[3,2-d]pyrimidin-4-ylamino)ethyl]-quinolin-2-yl}piperazin-1-yl)methanone;
- (4-{7-fluoro-8-methyl-3-[(1S)-1-(pyrido[3,2-d]pyrimidin-4-ylamino)ethyl]quinolin-2-yl}piperazin-1-yl)acetic acid;
- 1-(4-{8-chloro-3-[(1S)-1-(pyrido[3,2-d]pyrimidin-4-ylamino)ethyl]quinolin-2-yl}piperazin-1-yl)-2-hydroxyethanone;
- 1-(4-{8-chloro-3-[(1S)-1-(pyrido[3,2-d]pyrimidin-4-ylamino)ethyl]quinolin-2-yl}piperazin-1-yl)-2-(dimethylamino)ethanone;
- 2-(dimethylamino)-1-(4-{7-fluoro-8-methyl-3-[(1S)-1-(pyrido[3,2-d]pyrimidin-4-ylamino)ethyl]quinolin-2-yl}piperazin-1-yl)ethanone formic acid salt;
- 1-(4-{8-chloro-3-[(1S)-1-(pyrido[3,4-d]pyrimidin-4-ylamino)ethyl]quinolin-2-yl}piperazin-1-yl)-2-(dimethylamino)ethanone;
- 2-(dimethylamino)-1-(4-{7-fluoro-8-methyl-3-[(1S)-1-(pyrido[3,4-d]pyrimidin-4-ylamino)ethyl]quinolin-2-yl}piperazin-1-yl)ethanone;
- (4-{7-fluoro-8-methyl-3-[(1S)-1-(pyrido[3,4-d]pyrimidin-4-ylamino)ethyl]quinolin-2-yl}piperazin-1-yl)acetic acid;
- 2-(4-{8-chloro-3-[(1S)-1-(pyrido[3,2-d]pyrimidin-4-ylamino)ethyl]quinolin-2-yl}piperazin-1-yl)acetamide;
- 2-(4-{7-fluoro-8-methyl-3-[(1S)-1-(pyrido[3,2-d]pyrimidin-4-ylamino)ethyl]quinolin-2-yl}piperazin-1-yl)-N-methylacetamide;
- 2-(4-{8-chloro-3-[(1S)-1-(pyrido[3,2-d]pyrimidin-4-ylamino)ethyl]quinolin-2-yl}piperazin-1-yl)-N-methylacetamide; and
- 2-(4-{7-Fluoro-8-methyl-3-[(1S)-1-(pyrido[3,2-d]pyrimidin-4-ylamino)ethyl]quinolin-2-yl}piperazin-1-yl)acetamide;

and a pharmaceutically acceptable salt or N-oxide of any of the foregoing.

7. A pharmaceutical composition comprising a compound of formula (I) as defined in claim 1 or an N-oxide thereof, or a pharmaceutically acceptable salt thereof, in association with a pharmaceutically acceptable carrier.

8. A compound as claimed in claim 2 wherein the moiety of which M is the residue is selected from 4-(pyridin-2-yl)piperazin-1-yl, 4-(pyrazin-2-yl)piperazin-1-yl, 4-(2-hydroxyethyl)piperazin-1-yl, 3-oxopiperazin-1-yl, 4-acetylpiperazin-1-yl, 4-(ethylcarbonyl)piperazin-1-yl, 4-(tert-butylcarbonyl)piperazin-1-yl, 4-(hydroxyacetyl)piperazin-1-yl, 4-(dimethylaminoacetyl)-piperazin-1-yl, 4-(cyclopropylcarbonyl)piperazin-1-yl, 4-(carboxymethyl)piperazin-1-yl, 4-(methoxycarbonyl)piperazin-1-yl, 4-(aminocarbonyl)piperazin-1-yl, 4-(aminocarbonylmethyl)piperazin-1-yl and 4-(methylaminocarbonylmethyl)piperazin-1-yl.

9. A compound as claimed in claim 2 wherein $R^1$ represents hydrogen, halogen or $C_{1-6}$ alkyl.

10. A compound as claimed in claim 2 wherein $R^2$ represents hydrogen or halogen.

11. A pharmaceutical composition comprising a compound of formula (I) as defined in claim 2 or an N-oxide thereof, or a pharmaceutically acceptable salt thereof, in association with a pharmaceutically acceptable carrier.

* * * * *